(12) United States Patent
Kanda et al.

(10) Patent No.: US 10,292,577 B2
(45) Date of Patent: May 21, 2019

(54) IMAGE PROCESSING APPARATUS, METHOD, AND COMPUTER PROGRAM PRODUCT

(71) Applicant: Olympus Corporation, Hachioji-shi, Tokyo (JP)

(72) Inventors: Yamato Kanda, Hino (JP); Takashi Kono, Hachioji (JP); Masashi Hirota, Hachioji (JP)

(73) Assignee: Olympus Corporation, Tokyo (JP)

( * ) Notice: Subject to any disclaimer, the term of this patent is extended or adjusted under 35 U.S.C. 154(b) by 14 days.

(21) Appl. No.: 15/649,951

(22) Filed: Jul. 14, 2017

(65) Prior Publication Data
US 2017/0311782 A1 Nov. 2, 2017

Related U.S. Application Data

(63) Continuation of application No. PCT/JP2015/051873, filed on Jan. 23, 2015.

(51) Int. Cl.
| | |
|---|---|
| *G06T 7/00* | (2017.01) |
| *A61B 1/04* | (2006.01) |
| *G06T 7/11* | (2017.01) |
| *G06T 7/149* | (2017.01) |
| *A61B 1/05* | (2006.01) |
| *A61B 1/00* | (2006.01) |
| *A61B 1/045* | (2006.01) |

(52) U.S. Cl.
CPC ............ *A61B 1/04* (2013.01); *A61B 1/00009* (2013.01); *A61B 1/05* (2013.01); *G06T 7/0012* (2013.01);
(Continued)

(58) Field of Classification Search
CPC ......... A61B 1/04; A61B 1/00009; A61B 1/05; A61B 1/045; G06T 7/11; G06T 7/149;
(Continued)

(56) References Cited

U.S. PATENT DOCUMENTS

| | | |
|---|---|---|
| 2005/0010082 A1 | 1/2005 | Nishimura et al. |
| 2007/0173690 A1 | 7/2007 | Nishimura et al. |
| (Continued) | | |

FOREIGN PATENT DOCUMENTS

| | | |
|---|---|---|
| JP | 2003-093328 A | 4/2003 |
| JP | 2005-192880 A | 7/2005 |
| JP | 2007-244518 A | 9/2007 |

OTHER PUBLICATIONS

English Translation of International Search Report and Written Opinion dated Apr. 21, 2015 issued in PCT/JP2015/051873, 9 pages.

*Primary Examiner* — Ping Y Hsieh
(74) *Attorney, Agent, or Firm* — Matthew M. Eslami; Gerald P. Kazanjian

(57) ABSTRACT

Example embodiments of the present invention relate to an image processing apparatus. The apparatus may include a processor and memory storing instructions that when executed on the processor cause the processor to perform the operations of detecting a deep region of a duct in an image and extracting a plurality of contour edges of an inner wall of the duct in the image. The apparatus then may identify a plurality of convex regions among the plurality of contour edges, analyze a respective curvature of each of the plurality of convex regions to identify a convex direction for each of the plurality of convex regions, and detect, as an abnormal region, a convex region having a convex direction directed toward the deep region.

35 Claims, 17 Drawing Sheets

(52) U.S. Cl.
CPC ............... *G06T 7/11* (2017.01); *G06T 7/149* (2017.01); *A61B 1/045* (2013.01); *G06T 2207/10024* (2013.01); *G06T 2207/10068* (2013.01); *G06T 2207/30032* (2013.01); *G06T 2207/30092* (2013.01)

(58) Field of Classification Search
CPC ......... G06T 7/0012; G06T 2207/10068; G06T 2207/30032; G06T 2207/30092
See application file for complete search history.

(56) References Cited

U.S. PATENT DOCUMENTS

| | | | |
|---|---|---|---|
| 2007/0179338 A1 | 8/2007 | Nishimura et al. | |
| 2007/0191679 A1 | 8/2007 | Nishimura et al. | |
| 2007/0191681 A1 | 8/2007 | Nishimura et al. | |
| 2009/0074268 A1 | 3/2009 | Tanaka et al. | |
| 2012/0070049 A1* | 3/2012 | Iwase | G06T 7/0012 382/128 |
| 2013/0195340 A1* | 8/2013 | Iwase | G06K 9/00617 382/131 |
| 2015/0063641 A1* | 3/2015 | Kitamura | G06T 7/0014 382/103 |
| 2015/0206022 A1* | 7/2015 | Radha Krishna Rao | G06K 9/4604 382/128 |
| 2015/0320299 A1* | 11/2015 | Krupnik | A61B 1/00009 348/65 |
| 2016/0292875 A1* | 10/2016 | Kono | G06T 7/0012 |

* cited by examiner

IMAGE PROCESSING APPARATUS, METHOD, AND COMPUTER PROGRAM PRODUCT

CROSS-REFERENCE TO RELATED APPLICATION(S)

This application is a continuation application of PCT Application No. PCT/JP2015/051873 filed Jan. 23, 2015, which is hereby incorporated by reference in its entirety.

TECHNICAL FIELD

The present invention relates to an image processing device, an image processing method, and an image processing program, which perform image processing on an intraductal image.

BACKGROUND

A technique based on an edge line in an endoscopic image and pixel data around the edge to determine whether the edge is an abnormal tissue edge has been conventionally disclosed. For example, Japanese Patent Application Publication No. JP-A-2007-244518 discloses image analysis device and image analysis method.

SUMMARY

Example embodiments of the present invention relate to an image processing apparatus. The Apparatus comprises a processor and memory storing instructions that when executed on the processor cause the processor to perform the operations of detecting a deep region of a duct in an image, extracting a plurality of contour edges of an inner wall of the duct in the image, identifying a plurality of convex regions among the plurality of contour edges, analyzing a respective curvature of each of the plurality of convex regions to identify a convex direction for each of the plurality of convex regions, and detecting, as an abnormal region, a convex region having a convex direction directed toward the deep region.

Example embodiments of the present invention relate to a method. The method comprises detecting a deep region of a duct in an image, extracting a contour edge of an inner wall of the duct in the image, identifying a plurality of convex regions among the plurality of contour edges, analyzing a respective curvature of each of the plurality of convex regions to identify a convex direction for each of the plurality of convex regions, and detecting, as an abnormal region, a convex region having a convex direction directed toward a direction of the deep region.

Example embodiments of the present invention relate to a computer program product including a non-transitory computer readable medium having computer program code encoded thereon that when executed by a processor of a computer causes the computer to perform image processing. The computer program code comprises computer program code for detecting a deep region of a duct in an image, computer program code for extracting a contour edge of an inner wall of the duct in the image, computer program code for identifying a plurality of convex regions among the plurality of contour edges, computer program code for analyzing a respective curvature of each of the plurality of convex regions to identify a convex direction for each of the plurality of convex regions, and computer program code for detecting, as an abnormal region, a convex region having a convex direction directed toward a direction of the deep region.

BRIEF DESCRIPTION OF THE DRAWINGS

Objects, features, and advantages of embodiments disclosed herein may be better understood by referring to the following description in conjunction with the accompanying drawings. The drawings are not meant to limit the scope of the claims included herewith. For clarity, not every element may be labeled in every Figure. The drawings are not necessarily to scale, emphasis instead being placed upon illustrating embodiments, principles, and concepts. Thus, features and advantages of the present disclosure will become more apparent from the following detailed description of exemplary embodiments thereof taken in conjunction with the accompanying drawings.

DETAILED DESCRIPTION

As described in Japanese Patent Application Publication No. JP-A-2007-244518, the determination whether the edge is an abnormal tissue edge is made based on the presence or absence of an intersection between a pixel-value gradient vector (pixel-value lowering direction) in an inside peripheral position of an arc of the edge line, and the edge line. Specifically, when the pixel-value gradient vector and the edge line intersect with each other, the edge is determined to be a polyp, while when the pixel-value gradient vector and the edge line do not intersect with each other, the edge is determined to be a normal contour.

However, since the lowering of pixel values is caused due to shade and shadow near a mucosal fold edge in the endoscopic image, the pixel values of a mucosal surface located at the back of the mucosal fold edge often become higher. Therefore, when only the technique described in Japanese Patent Application Publication No. JP-A-2007-244518 is used, a pixel-value gradient vector of the mucosal surface, located in the inside peripheral position of the arc, namely at the back of the mucosal fold edge, may intersect with the mucosal fold edge even if the mucosal fold edge is a normal mucosal fold edge, resulting in an erroneous determination that the edge is an abnormal tissue edge.

The present invention has been made in view of the above problem, and it is an object thereof to provide an image processing device, an image processing method, and an image processing program, capable of detecting an abnormal tissue edge with high accuracy while suppressing an erroneous determination of a normal edge to be abnormal.

Means for Solving the Problems

According to the present invention, a contour edge region having a raised shape in the direction of a luminal deep region is detected as an abnormal region, so that the abnormal region can be detected with high accuracy while suppressing the erroneous detection of a normal contour edge as being abnormal.

Modes for carrying out the present invention (hereinafter called "embodiments") will be described below.

Figure 1:
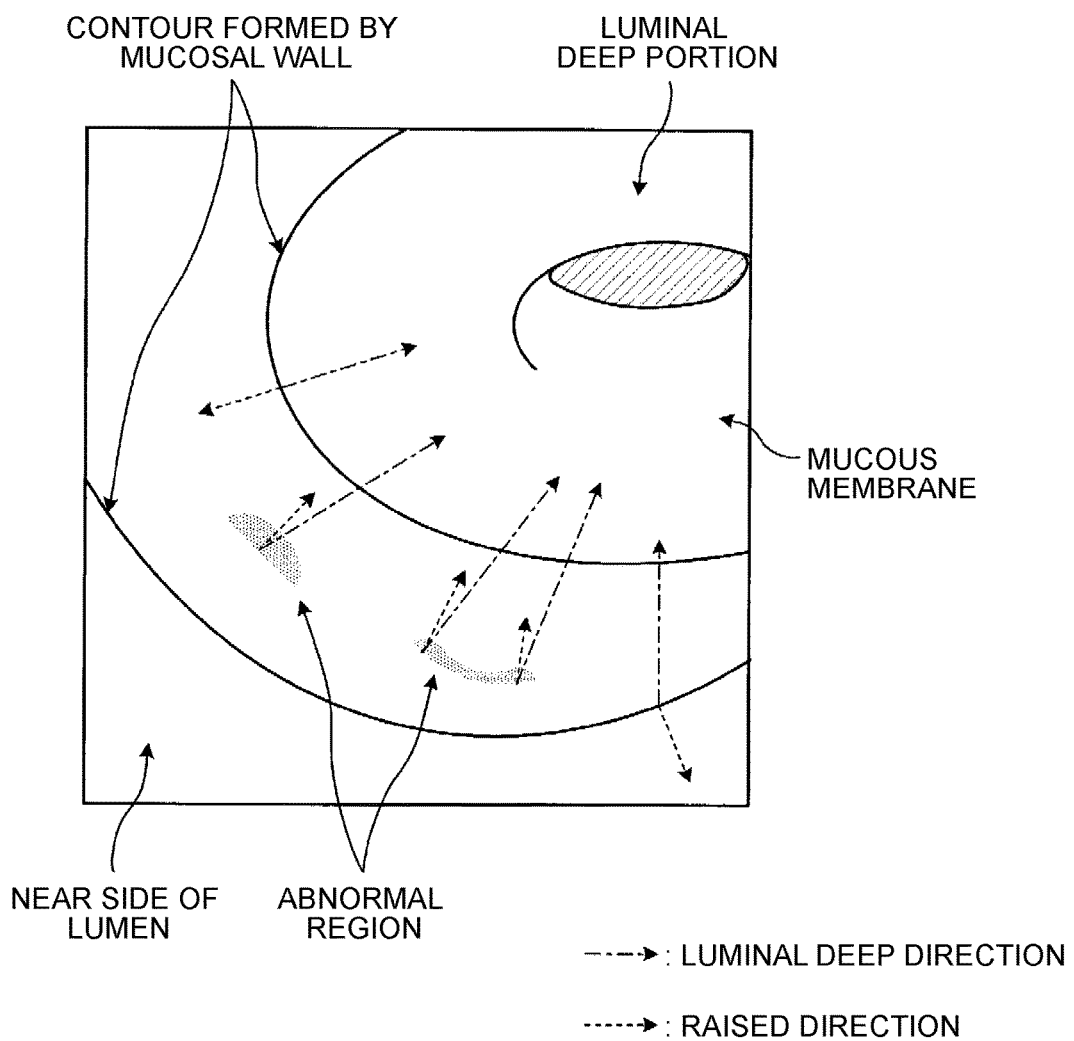
FIG. 1 is a diagram for describing an outline of embodiments of the present invention.

FIG. 1 is a diagram for describing an outline of embodiments of the present invention. Specifically, FIG. 1 is a diagram schematically illustrating, as an example of an intraductal image, an intraluminal image captured using an endoscope inserted into a living body to make an intravital observation. In general, the endoscope captures an image of a mucosal surface of the inner wall of a lumen from an oblique direction. Therefore, an area from a mucosal surface on a near side of the lumen close in image capturing distance to a mucosal surface of a luminal deep portion far in image capturing distance appears in the image captured using the endoscope as illustrated in FIG. 1, and an abnormal region sometimes appears in this area. A contour edge formed by a mucosal fold basically has a shape raised on a side opposite to a luminal deep direction, and a shape raised in the luminal deep direction is formed in the contour edge of the abnormal region. The image processing devices according to the embodiments focus attention on a difference between these raised shapes to detect the abnormal region. The intraluminal image captured using the endoscope is generally a color image having a pixel value for each of wavelength components of R (red), G (green), and B (blue) in each pixel position, but the present invention is not limited thereto.

Figure 2:
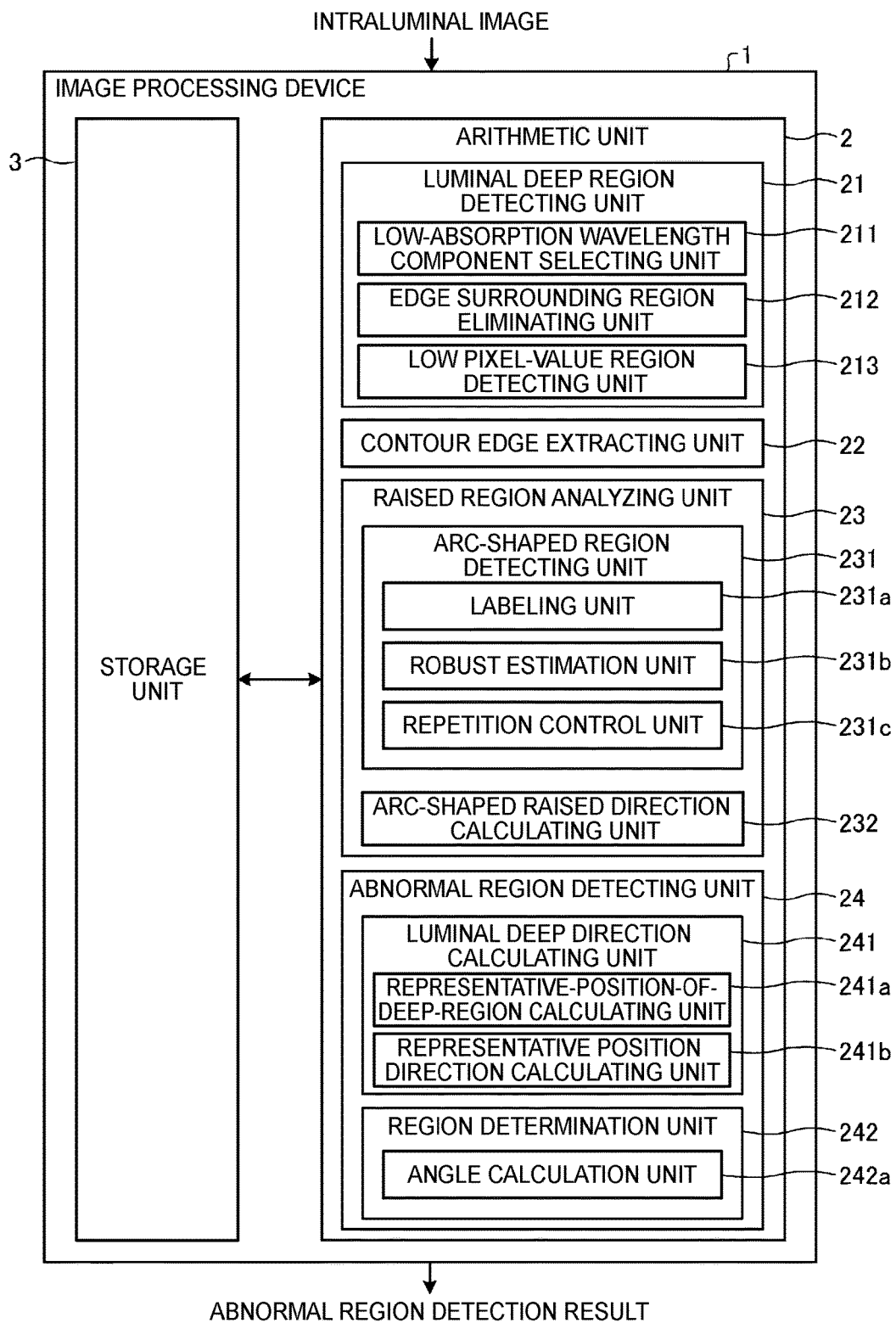
FIG. 2 is a block diagram illustrating the functional configuration of an image processing device according to Embodiment 1 of the present invention.

FIG. 2 is a block diagram illustrating the functional configuration of an image processing device according to Embodiment 1. An image processing device 1 illustrated in the figure has an arithmetic unit 2 and a storage unit 3.

The arithmetic unit 2 has a luminal deep region detecting unit 21 (as an example of a deep region detecting unit) that detects a luminal deep region based on information correlated with image capturing distance, a contour edge extracting unit 22 that extracts a contour edge of a mucosal wall of a lumen, a raised region analyzing unit 23 that analyzes a raised region in the contour edge and a raised direction of the raised region, and an abnormal region detecting unit 24 that detects, as an abnormal region, a raised region raised in the direction of the luminal deep region.

The luminal deep region detecting unit 21 has a low-absorption wavelength component selecting unit 211 that selects a low-absorption wavelength component whose degree of absorption/scattering in a living body is lowest, an edge surrounding region eliminating unit 212 that eliminates pixels of an edge surrounding region in an image of the low-absorption wavelength component, and a low pixel-value region detecting unit 213 that detects a region having relatively low pixel values in the image of the low-absorption wavelength component after the pixels of the edge surrounding region are eliminated.

A region in which the pixels detected by the low pixel-value region detecting unit 213 are present in a cluster is generally thought of as a luminal deep region. The luminal deep region detecting unit 21 performs known labeling processing (Reference: Labeling, "Digital Image Processing," p. 181, CG-ARTS Society) on the pixels detected by the low pixel-value region detecting unit 213 to detect, as the luminal deep region, a region having the largest area after connected pixels are put together into one region.

In the case of an image composed of R, G, and B components, the low-absorption wavelength component selecting unit 211 selects the R component as a component far away from a blood absorption band, with a long wavelength, and hardly affected by absorption and scattering in the living body. The low-absorption wavelength component selecting unit 211 can make such a selection to suppress the lowering of pixel values due to blood vessels and the like that appear in a mucosal surface so as to obtain pixel value information correlated most closely with the image capturing distance to the mucosal surface.

The edge surrounding region eliminating unit 212 applies, for example, known edge extraction processing (Reference:

Edge Extraction (p. 114) and Contour Extraction (p. 209), "Digital Image Processing," CG-ARTS Society) to identify an edge region, and then performs known expansion processing (Reference: Extraction/Contraction Process, "Digital Image Processing," p. 179, CG-ARTS Society) on the edge region to identify and eliminate surrounding regions). Thus, the edge surrounding region eliminating unit 212 eliminates the edge surrounding regions to be able to eliminate the mucous membrane of a luminal deep portion (the mucous membrane where illumination light is hard to reach so that the pixel value of a low-absorption wavelength component will be lowered) like a shaded portion around a contour edge of a mucosal fold, and a region with the risk of being detected erroneously.

The low pixel-value region detecting unit 213 detects pixels having relatively low pixel values and occupying a predetermined area ratio in the image of the low-absorption wavelength component after the edge surrounding regions are eliminated. Note that the low pixel-value region detecting unit 213 may detect pixels having pixel values less than or equal to a threshold value set based on a range of pixel values of the pixels in the image of the low-absorption wavelength component after the edge surrounding regions are eliminated.

The contour edge extracting unit 22 selects a low-absorption wavelength component (e.g., the R component) whose degree of absorption/scattering in the living body is lowest to perform edge extraction processing on an image of this wavelength component. The above-mentioned known edge extraction processing can also be applied to this edge extraction processing. The contour edge extracting unit 22 selects the low-absorption wavelength component to be able not to erroneously extract, as a contour edge, an edge formed by a blood vessel(s) or the like in a mucosal surface. Note, for example, that a contour edge extraction method disclosed in Japanese Patent Application Laid-Open No. 2014-104293, or edge extraction processing performed on obtained three-dimensional pixel-value information as disclosed in Japanese Patent Application Laid-Open No. 2012-11137 can also be applied to the contour edge extraction processing in Embodiment 1.

Figure 3:
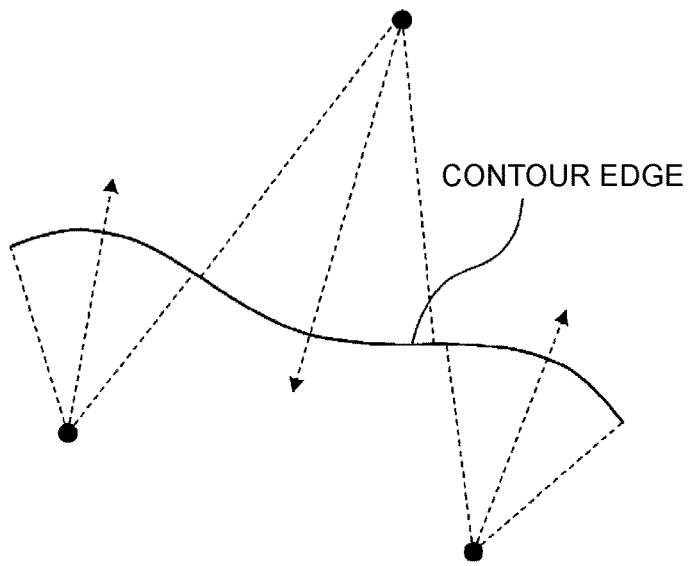
FIG. 3 is a diagram schematically illustrating an outline of processing performed by a raised region analyzing unit of the image processing device according to Embodiment 1 of the present invention.

The raised region analyzing unit 23 has an arc-shaped region detecting unit 231 that detects an arc-shaped region in the contour edge and an arc-shaped raised direction calculating unit 232 that calculates a raised direction of the detected arc-shaped region. FIG. 3 is a diagram schematically illustrating an outline of processing performed by the raised region analyzing unit 23. When there is a waved contour edge in an image as illustrated in FIG. 3, the arc-shaped region detecting unit 231 analyzes the contour edge as three raised regions while detecting arc-shaped regions sequentially, and the raised region analyzing unit 23 determines the raised directions of the three raised regions, respectively.

The arc-shaped region detecting unit 231 has a labeling unit 231a that labels each contour edge so that the same label will be put on the contour edges to be connected, a robust estimation unit 231b that detects an arc-shaped (=raised) region by robust estimation based on pixels in the contour edges of the same label, and a repetition control unit 231c that determines a difference in magnitude between the area of any contour edge region other than that detected as an arc-shaped region, and a predetermined threshold value.

The labeling unit 231a puts contour edge pixels to be connected together, where the contour edge pixels are to be processed in the detection of arc-shaped regions at the subsequent stage. The labeling unit 231a performs, for example, the known labeling processing mentioned above. This can improve the detection accuracy and the processing speed.

The robust estimation unit 231b extracts, for example, at least three points or more of pixels in the contour edges of the same label at random to fit a circle to the coordinates of the extracted pixels by the least-square method. Then, the robust estimation unit 231b determines a distance between the circle and each of the pixels in each of the contour edges of the same label to calculate the number of pixels (pixel count) each of whose distances is less than or equal to a predetermined value. After these processes of "pixel extraction," "circle fitting," and "calculation of the pixel count with distances less than or equal to the predetermined value" are repeatedly executed predetermined times, a circle containing the largest pixel count, where distance to each pixel is less than or equal to the predetermined value, is finally selected to detect, as an arc-shaped region, pixels each of whose distances to the circle is less than or equal to the predetermined value. Note that the method of the robust estimation made by the robust estimation unit 231b is not limited to that described here, and any other known robust estimation method can be adopted.

For all arc-shaped regions detected, the arc-shaped raised direction calculating unit 232 sets a direction from the chord toward the arc of each arc-shaped region as the raised direction of the arc-shaped region. More preferably, the arc-shaped raised direction calculating unit 232 calculates a direction from the center of curvature of the arc-shaped region toward the midpoint of the arc of the arc-shaped region to set this direction as the raised direction of the arc-shaped region. Alternatively, the arc-shaped raised direction calculating unit 232 may calculate a direction from the midpoint of the arc toward the center of curvature of the arc-shaped region to set a direction opposite to the calculated direction as the raised direction.

The abnormal region detecting unit 24 has a luminal deep direction calculating unit 241 (an example of a deep direction calculating unit) that calculates a luminal deep direction based on the detection result of the luminal deep region and the analysis result of the raised region, and a region determination unit 242 that determines a raised region raised in the luminal deep direction.

The luminal deep direction calculating unit 241 has a representative-position-of-deep-region calculating unit 241a that calculates a representative position of a luminal deep region (an example of a deep region), and a representative position direction calculating unit 241b that calculates, as a representative position direction, a direction from the representative position of each raised region to the representative position of the luminal deep region.

The representative position calculated by the representative-position-of-deep-region calculating unit 241a or the representative position direction calculating unit 241b may be any position as long as the position represents the luminal deep region or each raised region in the image. As such a representative position, for example, the center of gravity of each region, the center of a rectangle region circumscribing each region, or the like can be adopted.

The region determination unit 242 has an angle calculation unit 242a that calculates an angle (≤180°) between the raised direction of each raised region and the luminal deep direction.

The arithmetic unit 2 is configured using a general-purpose processor such as a CPU (Central Processing Unit), or a special-purpose processor such as any of various arithmetic circuits executing specific functions like an ASI (Application Specific Integrated Circuit). When the arithmetic unit 2 is the general-purpose processor, the arithmetic unit 2 reads each of various programs stored in the storage unit 3 to give instructions or transfer data to each of the units constituting the image processing device 1 in order to control the entire operation of the image processing device 1 as a whole. When the arithmetic unit 2 is a special-purpose processor, the processor may execute various processes alone or execute various processes using various data and the like stored in the storage unit 3 in such a manner that the processor and the storage unit 3 cooperate or be combined with each other.

The storage unit 3 is implemented by each of various IC memories, such as a ROM (Read Only Memory) or a RAM (Random Access Memory), a hard disk incorporated or connected through a data communication terminal, or an information recording unit such as a CD-ROM and a reading unit therefor. The storage unit 3 stores a program for operating the image processing device 1 and causing the image processing device 1 to execute various functions, data used while this program is running, and the like, as well as image data on intraluminal images acquired by the image processing device 1. Specifically, the storage unit 3 stores an image processing program according to the Embodiment and various parameters such as threshold values used in the image processing.

Various programs such as the image processing program recorded in the storage unit 3 can also be recorded on a computer readable recording medium. Further, the various programs may be recorded in the storage unit 3 or on the recording medium before the shipment of a computer or the recording medium as a product, or may be downloaded through a communication network. The "communication network" here is implemented, for example, by an existing public line network, LAN (Local Area Network), WAN (Wide Area Network), or the like regardless of wired or wireless.

The image processing device 1 having the above configuration may be realized using one computer, or two or more computers. In the latter case, the computers can cooperate with each other to perform processing while exchanging data through a communication network. The "computers" here can be composed of a general-purpose personal computer, a server, a virtual computer, and the like.

A processor as part of an endoscope system, introduced into a subject body to observe the inside of the subject body, to control the entire endoscope system can also have the features of the image processing device 1 described above.

Figure 4:
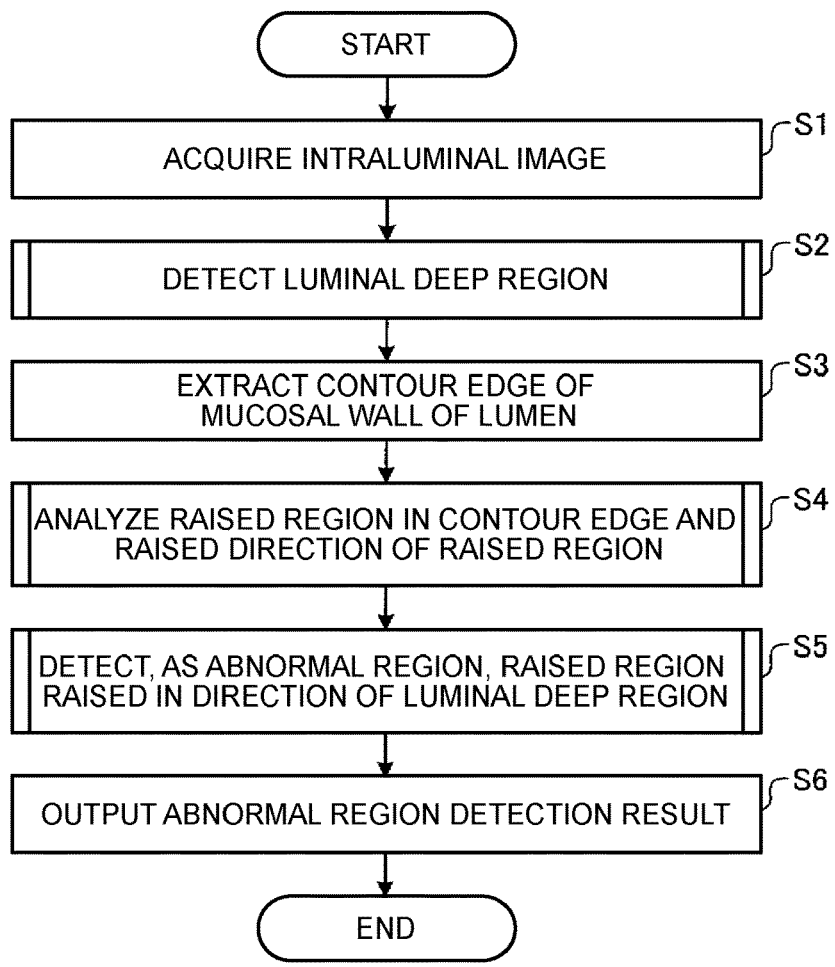
FIG. 4 is a flowchart illustrating an outline of processing performed by the image processing device according to Embodiment 1 of the present invention.

FIG. 4 is a flowchart illustrating an outline of processing performed by the image processing device 1. First, in step S1, the arithmetic unit 2 acquires an intraluminal image to be processed (step S1).

Figure 5:
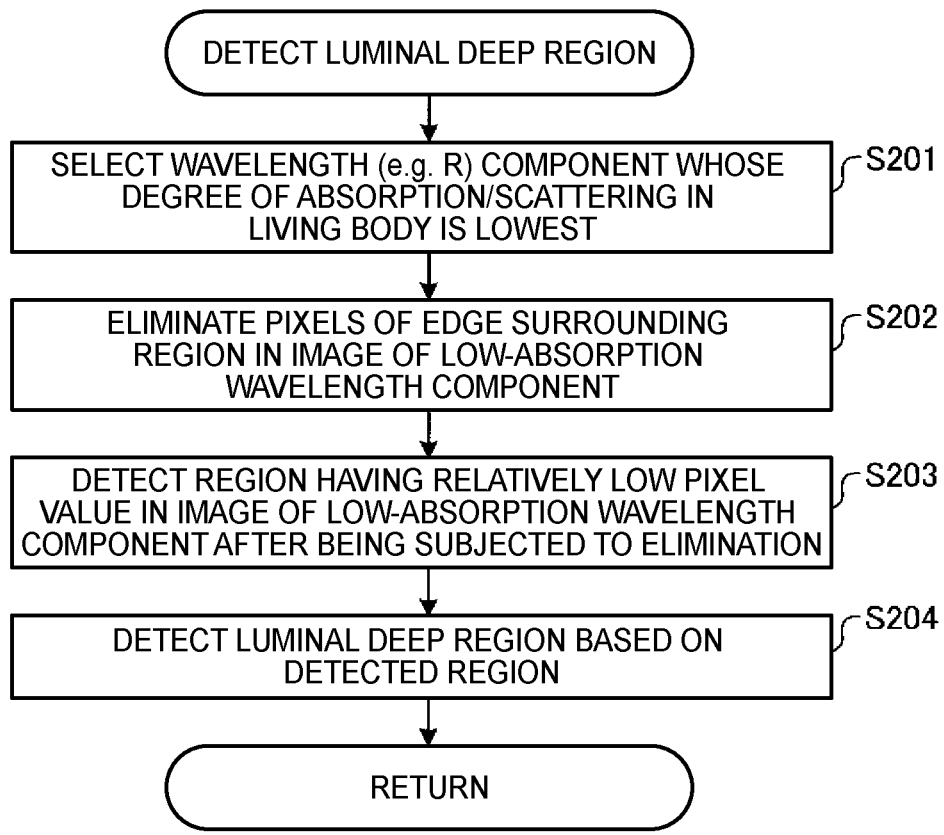
FIG. 5 is a flowchart illustrating an outline of processing performed by a luminal deep region detecting unit of the image processing device according to Embodiment 1 of the present invention.

In step S2, the luminal deep region detecting unit 21 detects a luminal deep region (step S2). FIG. 5 is a flowchart illustrating an outline of processing performed by the luminal deep region detecting unit 21. The processing performed by the luminal deep region detecting unit 21 will be described below with reference to FIG. 5.

In FIG. 5, the low-absorption wavelength component selecting unit 211 first selects a low-absorption wavelength component whose degree of absorption/scattering in the living body is lowest (step S201). For example, in the case of an image composed of R, G, and B components, the low-absorption wavelength component selecting unit 211 selects the R component as mentioned above.

After that, the edge surrounding region eliminating unit 212 eliminates pixels of an edge surrounding region in an image of the low-absorption wavelength component (step S202). This can prevent the edge surrounding region from being erroneously detected as a luminal deep region.

After that, the low pixel-value region detecting unit 213 detects a region having a relatively low pixel value in the image of the low-absorption wavelength component after being subjected to the elimination processing (step S203).

Then, based on the region detected by the low pixel-value region detecting unit 213, the luminal deep region detecting unit 21 performs known labeling processing or the like to detect a luminal deep region (step S204). Thus, the luminal deep region detection processing by the luminal deep region detecting unit 21 is ended.

In step S3 following step S2, the contour edge extracting unit 22 extracts the contour edge of a mucosal wall of a lumen (step S3). The contour edge extracting unit 22 selects a low-absorption wavelength component (e.g., the R component) whose degree of absorption/scattering in the living body is lowest, and performs the above-mentioned edge extraction processing on an image of this wavelength component.

In step S4, the raised region analyzing unit 23 analyzes a raised region in the contour edge and the raised direction of the raised region (step S4). When the contour edge illustrated in FIG. 3 exists in the image, the arc-shaped region detecting unit 231 sequentially detects and analyzes arc-shaped regions as three raised regions as mentioned above. After that, the raised region analyzing unit 23 determines the raised directions of the tree raised regions, respectively.

Figure 6:
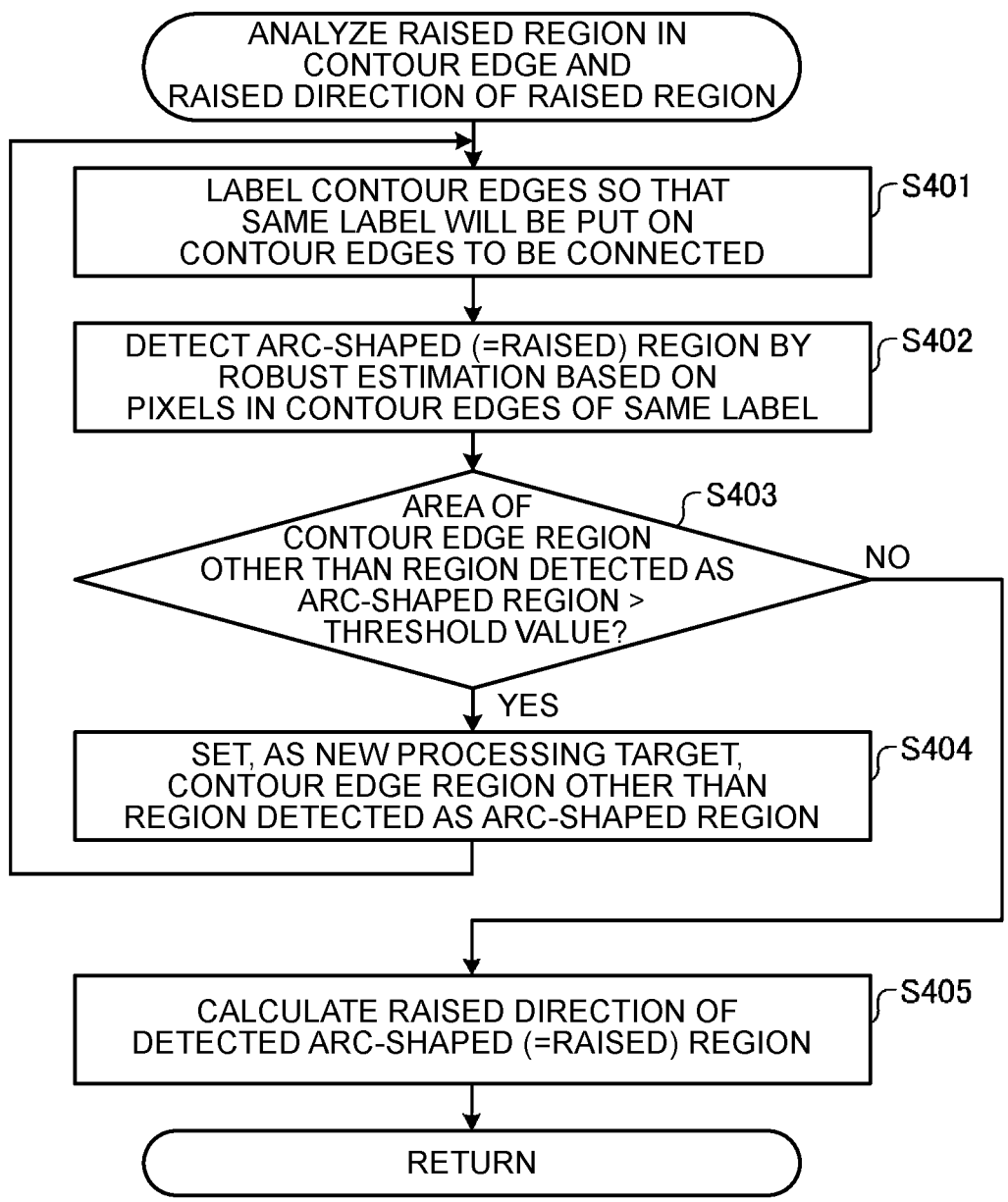
FIG. 6 is a flowchart illustrating an outline of raised region analysis processing performed by a raised region analyzing unit of the image processing device according to Embodiment 1 of the present invention.

FIG. 6 is a flowchart illustrating an outline of raised region analysis processing performed by the raised region analyzing unit 23. In the following, the outline of the raised region analysis processing will be described with reference to FIG. 6. First, the labeling unit 231*a* labels each contour edge so that the same label will be put on contour edges to be connected (step S401).

Then, the robust estimation unit 231*b* detects an arc-shaped (=raised) region by robust estimation based on pixels in the contour edges of the same label (step S402). The robust estimation unit 231*b* detects arc-shaped regions for all labeled contour edges.

After that, the repetition control unit 231*c* determines a difference in magnitude between the area of any contour edge region other than that detected as an arc-shaped region, and a predetermined threshold value (step S403). As a result of the determination, when the area of the contour edge region is larger than the threshold value (Yes in step S403), the raised region analyzing unit 23 sets the contour edge region other than that detected as the arc-shaped region as a new processing target (step S404), and the procedure returns to step S401. On the other hand, when the area of the contour edge region other than that detected as the arc-shaped region is less than or equal to the predetermined threshold value (No in step S403), the raised region analyzing unit 23 completes the detection of arc-shaped regions, and the procedure proceeds to step S405.

In step S405, the arc-shaped raised direction calculating unit 232 calculates a raised direction of the detected arc-shaped (=raised) region (step S405). Thus, the raised region analysis processing by the raised region analyzing unit 23 is ended.

In Embodiment 1, the method of using labeling and robust estimation in the detection of arc-shaped regions is illustrated, but the robust estimation may be repeatedly performed on all contour edge pixels without performing labeling. Further, a circular Hough transform disclosed in Japanese Patent Application Publication No. JP-A-2007-

244519 may be used. In addition, ellipse fitting rather than circle fitting may be performed in the robust estimation.

Figure 7:
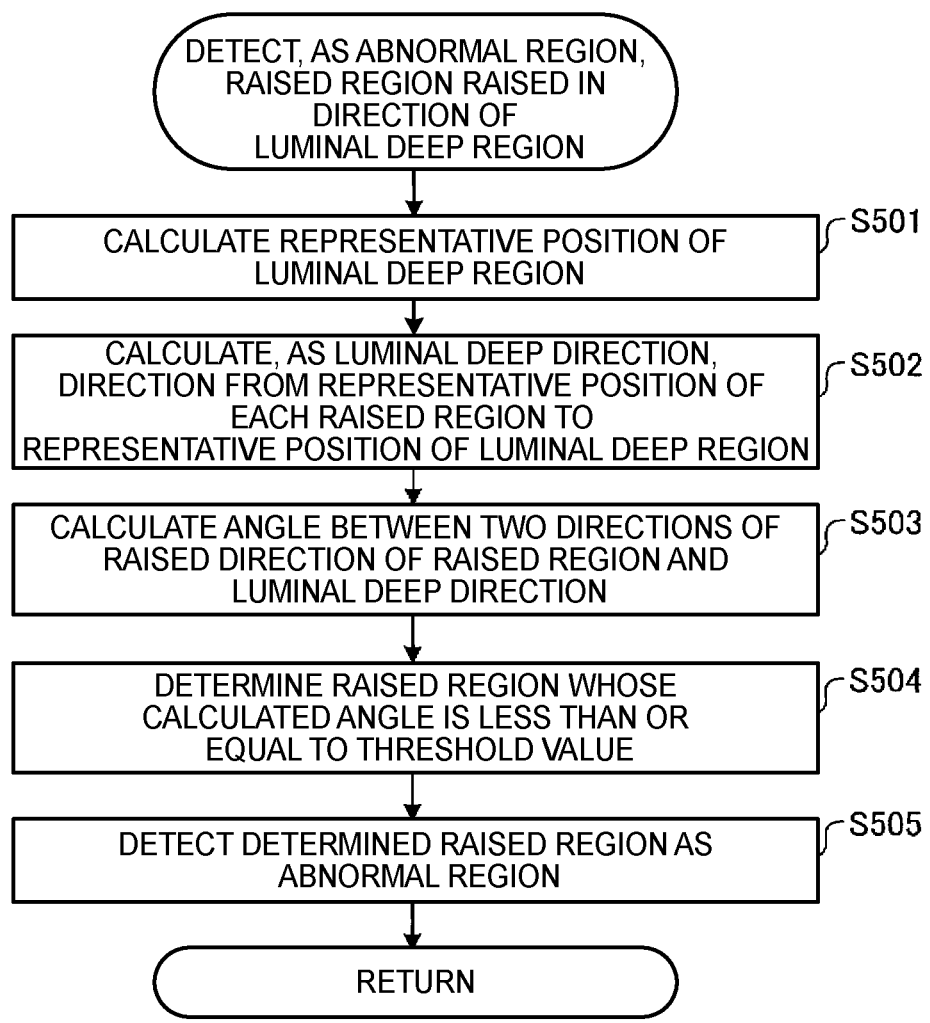
FIG. 7 is a flowchart illustrating an outline of processing performed by an abnormal region detecting unit of the image processing device according to Embodiment 1 of the present invention.

In step S5 following step S4, the abnormal region detecting unit 24 detects, as an abnormal region, a raised region raised in the direction of the luminal deep region (step S5). FIG. 7 is a flowchart illustrating an outline of processing performed by the abnormal region detecting unit 24. The following will describe the processing by the abnormal region detecting unit 24 with reference to FIG. 7.

First, the representative-position-of-deep-region calculating unit 241a in the luminal deep direction calculating unit 241 calculates a representative position of the luminal deep region determined in step S2 (step S501).

Then, the representative position direction calculating unit 241b calculates, as a luminal deep direction, the direction from the representative position of each raised region determined in step S4 to the representative position of the luminal deep region (step S502). As the representative position of the raised region, for example, the midpoint of an arc or the midpoint of a chord can be used as well as the center of gravity mentioned above.

After that, the angle calculation unit 242a in the region determination unit 242 calculates, for each raised region, an angle between the raised direction of the raised region and the luminal deep direction (step S503).

Then, the region determination unit 242 determines a region, whose angle calculated by the angle calculation unit 242a is less than or equal to a predetermined threshold value, to be the raised region (step S504). This threshold value is set, for example, as a value less than or equal to 90°.

Finally, the abnormal region detecting unit 24 detects the determined raised region as an abnormal region (step S505). Thus, the abnormal region detection processing by the abnormal region detecting unit 24 is ended.

In step S6 following step S5, the arithmetic unit 2 outputs the abnormal region detection result (step S6). Thus, a series of processing performed by the image processing device 1 is ended.

According to Embodiment 1 of the present invention described above, a contour edge region having a raised shape in the direction of the luminal deep region is detected as an abnormal region. Therefore, the abnormal region, i.e., an abnormal tissue edge can be detected with high accuracy while suppressing the erroneous detection of a normal contour edge as being abnormal.

Further, according to Embodiment 1, a low pixel-value region is detected after a low-absorption wavelength component is selected and an edge surrounding region(s) is eliminated. Therefore, a luminal deep region can be detected with high accuracy while suppressing the influence of shade and shadow of blood vessels and fold edges.

Further, according to Embodiment 1, an arc-shaped region in a contour edge is detected and the direction of the arc-shaped region is calculated. Therefore, the detection of a raised region in the contour edge and the calculation of the direction can be performed with high accuracy.

Further, according to Embodiment 1, labeling and robust estimation of the contour edge are repeated, so that plural arc shapes in the contour edge can be detected with high accuracy at high speed.

In Embodiment 1, the method of detecting the luminal deep region based on pixel values correlated with the image capturing distance is illustrated, but the luminal deep region may also be detected by using, for example, a luminal deep direction detecting method disclosed in Japanese Patent Application Laid-Open No. 2003-93328.

Figure 8:
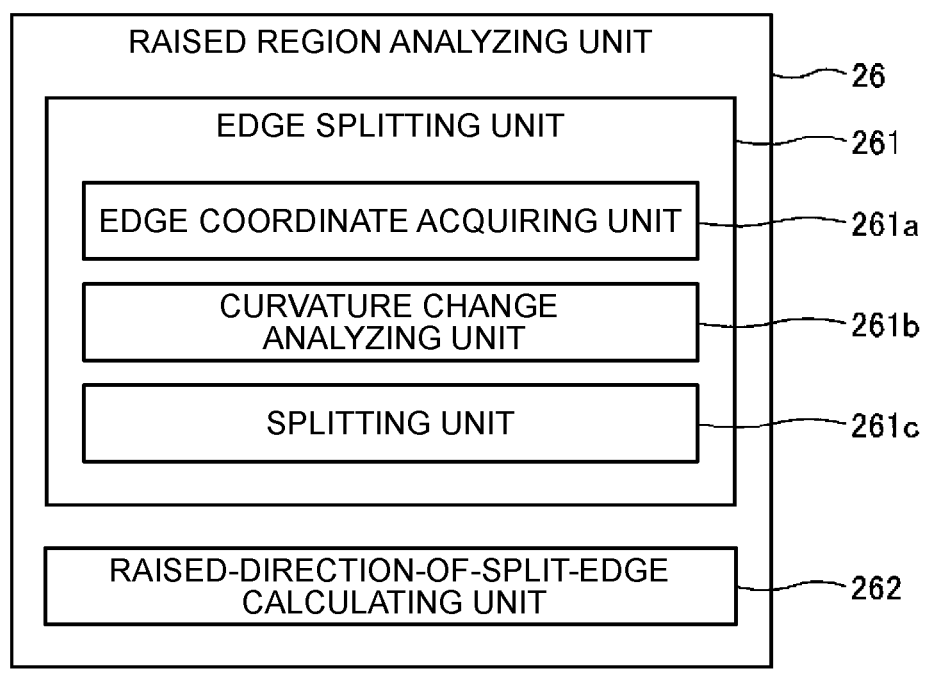
FIG. 8 is a block diagram illustrating the functional configuration of a raised region analyzing unit provided in an image processing device according to Variation 1 of Embodiment 1 of the present invention.

FIG. 8 is a block diagram illustrating the functional configuration of a raised region analyzing unit provided in an image processing device according to Variation 1 of Embodiment 1. A raised region analyzing unit 26 illustrated in the figure has an edge splitting unit 261 that splits a contour edge based on curved directions of the contour edge, and a raised-direction-of-split-edge calculating unit 262 that calculates the raised direction of each edge (split edge) after being split. The functional configuration of the image processing device is the same as the functional configuration of the image processing device 1 described in Embodiment 1 except for the raised region analyzing unit 26.

The edge splitting unit 261 has an edge coordinate acquiring unit 261a that acquires the coordinates of respective pixels forming the edge in order of connection, a curvature change analyzing unit 261b that analyzes a change in signed curvature with respect to the contour edge based on the coordinates of sample pixels placed at predetermined intervals along the acquired edge coordinates, and a splitting unit 261c that splits the contour edge at positions of sign inversion of the signed curvature.

The edge coordinate acquiring unit 261a acquires edge coordinates using, for example, known contour tracing processing (Reference: Contour Tracing, Digital Image Processing, p. 178, CG-ARTS Society).

A signed curvature k analyzed by the curvature change analyzing unit 261b is calculated by the following equation (1) based on the coordinates (x0, y0), (x1, y1), and (x2, y2) of three sample pixels placed at predetermined intervals (equal intervals):

[Math. 1]

$$k = \left(1 + \left(\frac{y2 - y0}{x2 - x0}\right)^2\right)^{\frac{3}{2}} \left(\frac{(y2 - y1) - (y1 - y0)}{(x2 - x1) - (x1 - x0)}\right) \quad (1)$$

The inversion of the sign of the signed curvature k corresponds to a change in the curved direction of the contour edge. The curvature change analyzing unit 261b calculates the coordinates of the sample pixels while shifting them along the edge coordinates to analyze the signed curvature k accordingly. Note that the interval between adjacent sample pixels may be decided adaptively, for example, depending on the distance from an image capturing plane determined based, for example, on the brightness of the low-absorption wavelength component.

Figure 9:
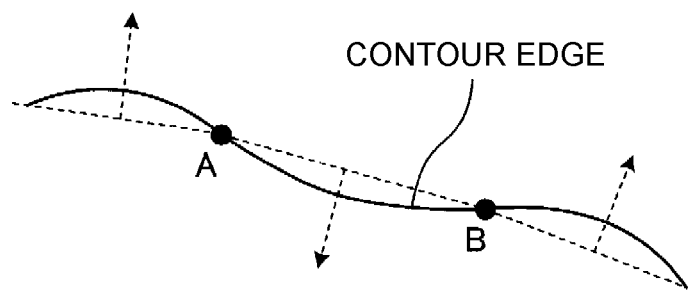
FIG. 9 is a diagram schematically illustrating an outline of contour edge splitting processing performed by a splitting unit of the image processing device according to Variation 1 of Embodiment 1 of the present invention.

FIG. 9 is a diagram schematically illustrating an outline of contour edge splitting processing performed by the splitting unit 261c. When a waved contour edge as illustrated in FIG. 9 exists, the splitting unit 261c splits the contour edge into three regions by setting two points A, B corresponding to wave nodes as boundaries.

The raised-direction-of-split-edge calculating unit 262 calculates, for all split edges, a direction of passing through each split edge from a line segment connecting both ends of the edge as the raised direction of the split edge. More preferably, the raised-direction-of-split-edge calculating unit 262 calculates, as the raised direction of the split edge, a direction from a midpoint of the line segment connecting both ends of the edge to a midpoint on the split edge (midpoint of the length of the split edge). For example, in the case of the contour edge illustrated in FIG. 9, the raised-direction-of-split-edge calculating unit 262 analyzes each of three split, raised regions to determine the raised direction of each raised region.

Figure 10:
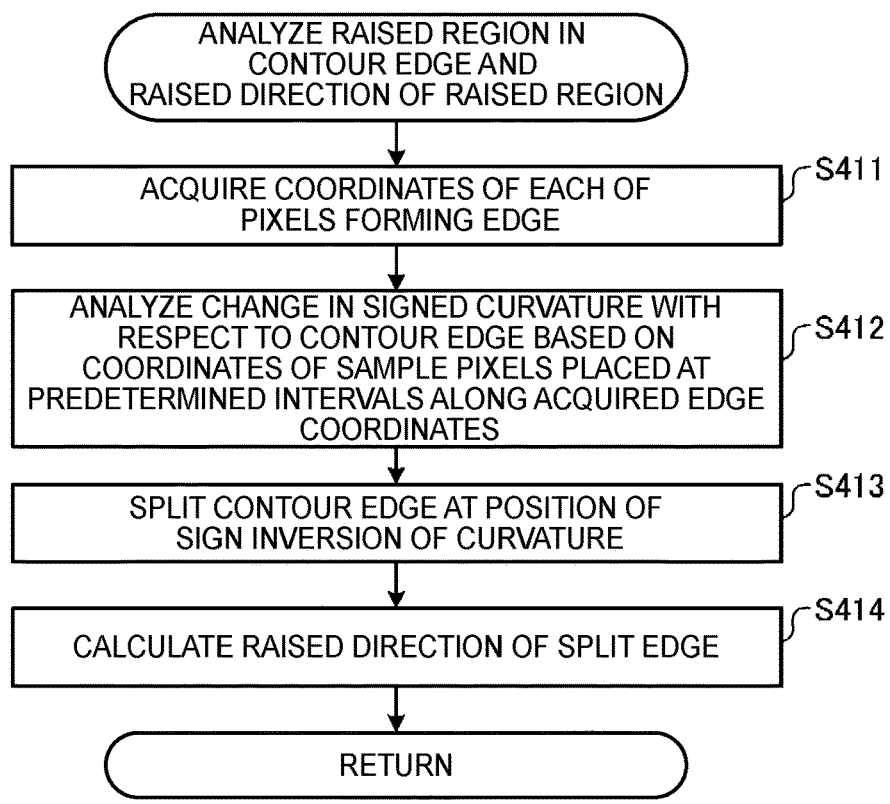
FIG. 10 is a flowchart illustrating an outline of processing performed by the raised region analyzing unit provided in the image processing device according to Variation 1 of Embodiment 1 of the present invention.

FIG. 10 is a flowchart illustrating an outline of processing performed by the raised region analyzing unit 26. First, the edge coordinate acquiring unit 261a acquires the coordinates of each of pixels forming each edge in order of connection (step S411).

Then, the curvature change analyzing unit 261b analyzes a change in signed curvature with respect to the contour edge based on the coordinates of three sample pixels placed at predetermined intervals along the acquired edge coordinates (step S412).

After that, the splitting unit 261c splits the contour edge at a position(s) of sign inversion of the signed curvature (step S413).

The raised region analyzing unit 26 executes processing steps S411 to S413 on all contour edges.

Then, the raised-direction-of-split-edge calculating unit 262 calculates the raised direction of the split edge (step S414). Thus, the raised region analysis processing by the raised region analyzing unit 26 is ended.

In Variation 1, the method of splitting an edge based on the signed curvature k is illustrated, but the split position may be determined based on a change in cross product of two vectors determined in such a manner that, among three points (x0, y0), (x1, y1), and (x2, y2), one vector has point (x1, y1) as a base point and point (x0, y0) as an end point, and the other vector has point (x1, y1) as the base point and point (x2, y2) as the end point.

In Variation 1, for example, a midpoint on each split edge, a point with the greatest curvature on the split edge, or the midpoint of a line segment connecting the end points of the split edge can be used as the representative position of the raised region.

According to Variation 1 of Embodiment 1 described above, a contour edge region having a raised shape in the direction of the luminal deep region is detected as an abnormal region. Therefore, the abnormal region can be detected with high accuracy while suppressing the erroneous detection of a normal contour edge as being abnormal.

Further, according to Variation 1, a contour edge is split based on each curved direction to calculate a raised direction of each split edge. Therefore, even when two or more raised shapes appear in the contour edge, the detection of each raised region and calculation of the direction can be performed with high accuracy.

Figure 11:
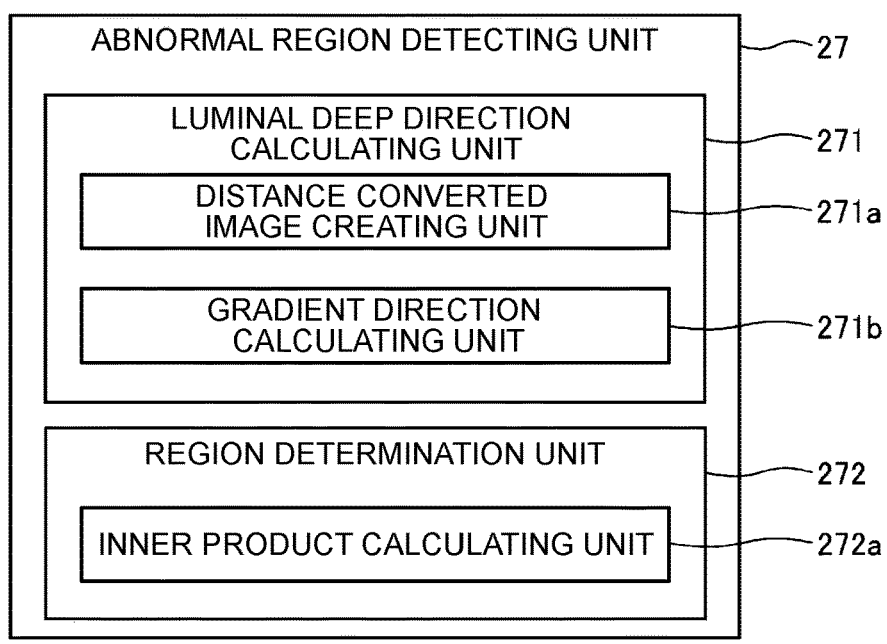
FIG. 11 is a block diagram illustrating the functional configuration of an abnormal region detecting unit provided in an image processing device according to Variation 2 of Embodiment 1 of the present invention.

FIG. 11 is a block diagram illustrating the functional configuration of an abnormal region detecting unit provided in an image processing device according to Variation 2 of Embodiment 1. An abnormal region detecting unit 27 illustrated in the figure has a luminal deep direction calculating unit 271 that calculates a luminal deep direction based on the detection result of a luminal deep region and the raised region analysis result, and a region determination unit 272 that determines a raised region raised in a luminal deep direction. The functional configuration of the image processing device is the same as the functional configuration of the image processing device 1 described in Embodiment 1 except for the abnormal region detecting unit 27.

The luminal deep direction calculating unit 271 has a distance converted image creating unit 271a that creates a distance converted image from the luminal deep region, and a gradient direction calculating unit 271b that calculates, as the luminal deep direction, a gradient direction of the distance converted image at a representative position of each raised region.

The distance converted image creating unit 271a creates a distance converted image by using, for example, known distance conversion (Reference: Distance Conversion and Skeleton Extraction, "Image Analysis Handbook," Tokyo University Press, p. 576).

The region determination unit 272 has an inner product calculating unit 272a that calculates, for each raised region, the inner product of unit directional vectors in two directions of the raised direction of the raised region and a luminal deep direction. The inner product of unit directional vectors is 1 in the case of the same direction, 0 in the case of being orthogonal, and −1 in the case of opposite directions.

Figure 12:
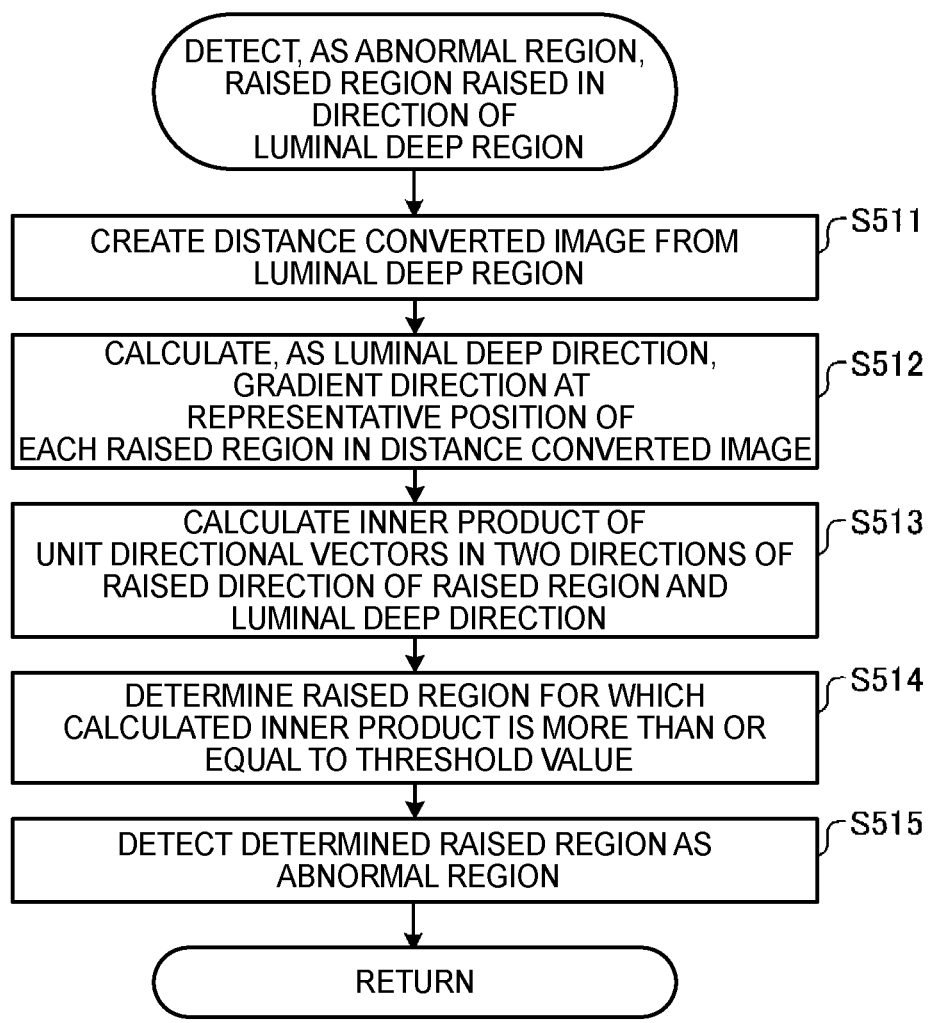
FIG. 12 is a flowchart illustrating an outline of processing performed by the abnormal region detecting unit provided in the image processing device according to Variation 2 of Embodiment 1 of the present invention.

FIG. 12 is a flowchart illustrating an outline of processing performed by the abnormal region detecting unit 27. The distance converted image creating unit 271a creates a distance converted image from a luminal deep region (step S511).

Then, the gradient direction calculating unit 271b calculates, as a luminal deep direction, a gradient direction of the distance converted image at a representative position of each raised region (step S512).

After that, the inner product calculating unit 272a calculates, for each raised region, an inner product of unit directional vectors in two directions of a raised direction of the raised region and the luminal deep direction (step S513).

Then, the region determination unit 272 determines a raised region for which the inner product is more than or equal to a predetermined threshold value (step S514).

Finally, the abnormal region detecting unit 27 detects the determined raised region as an abnormal region (step S515). Thus, abnormal region detection processing by the abnormal region detecting unit 27 is ended.

According to Variation 2 of Embodiment 1 described above, the distance converted image from the luminal deep region is used to determine the luminal deep direction. Therefore, even when the luminal deep portion has an elongate shape, the luminal deep direction can be determined with high accuracy.

In Embodiment 2 of the present invention, attention is focused on a difference in dimensions between raised regions contained in a contour edge to further increase the detection accuracy of an abnormal region.

Figure 13:
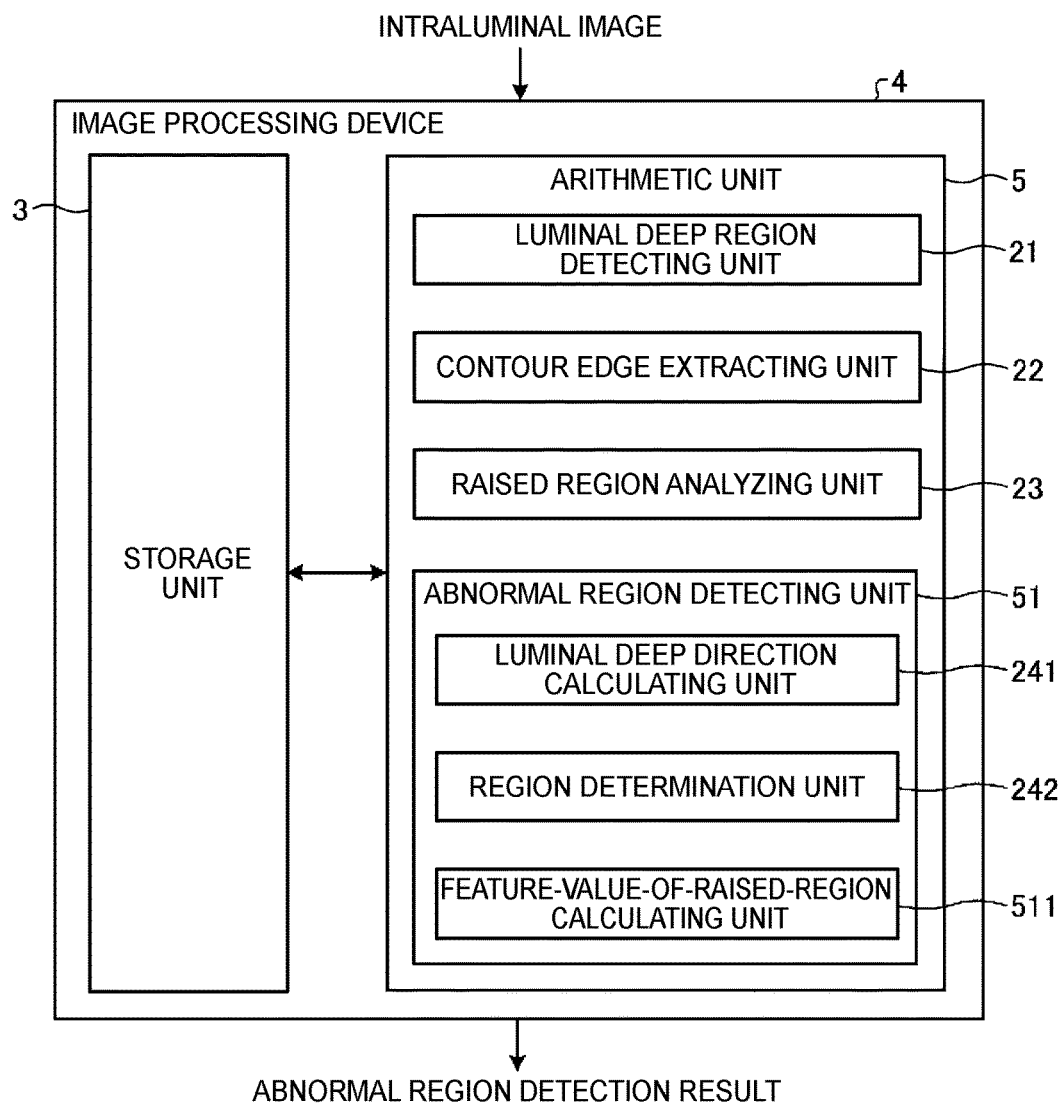
FIG. 13 is a block diagram illustrating the functional configuration of an image processing device according to Embodiment 2 of the present invention.

FIG. 13 is a block diagram illustrating the functional configuration of an image processing device according to Embodiment 2. An image processing device 4 illustrated in the figure includes an arithmetic unit 5 and a storage unit 3. In the following description, like components as those in the arithmetic unit 2 of the image processing device 1 according to Embodiment 1 are given the same reference numerals.

The arithmetic unit 5 has a luminal deep region detecting unit 21, a contour edge extracting unit 22, a raised region analyzing unit 23, and an abnormal region detecting unit 51. The abnormal region detecting unit 51 has a luminal deep direction calculating unit 241, a region determination unit 242, and a feature-value-of-raised-region calculating unit 511 that calculates the feature value of a raised region.

The feature value of a raised shape to be calculated by the feature-value-of-raised-region calculating unit 511 is the length or area of a raised region, a value correlated with the raised amount, or the like. Here, the value correlated with the raised amount is distance between a line segment connecting both ends of the raised region and a line segment parallel to the line segment and tangent to the raised region, a curvature when an arc shape is fitted to the raised region, a curvature radius, or the like. A raised region having a short length, a small area, a small raised amount, or the like is likely to be noise. Therefore, the feature-value-of-raised-region calculating unit 511 calculates the feature values of raised shapes mentioned above in order not to detect these regions erroneously as abnormal regions.

Figure 14:
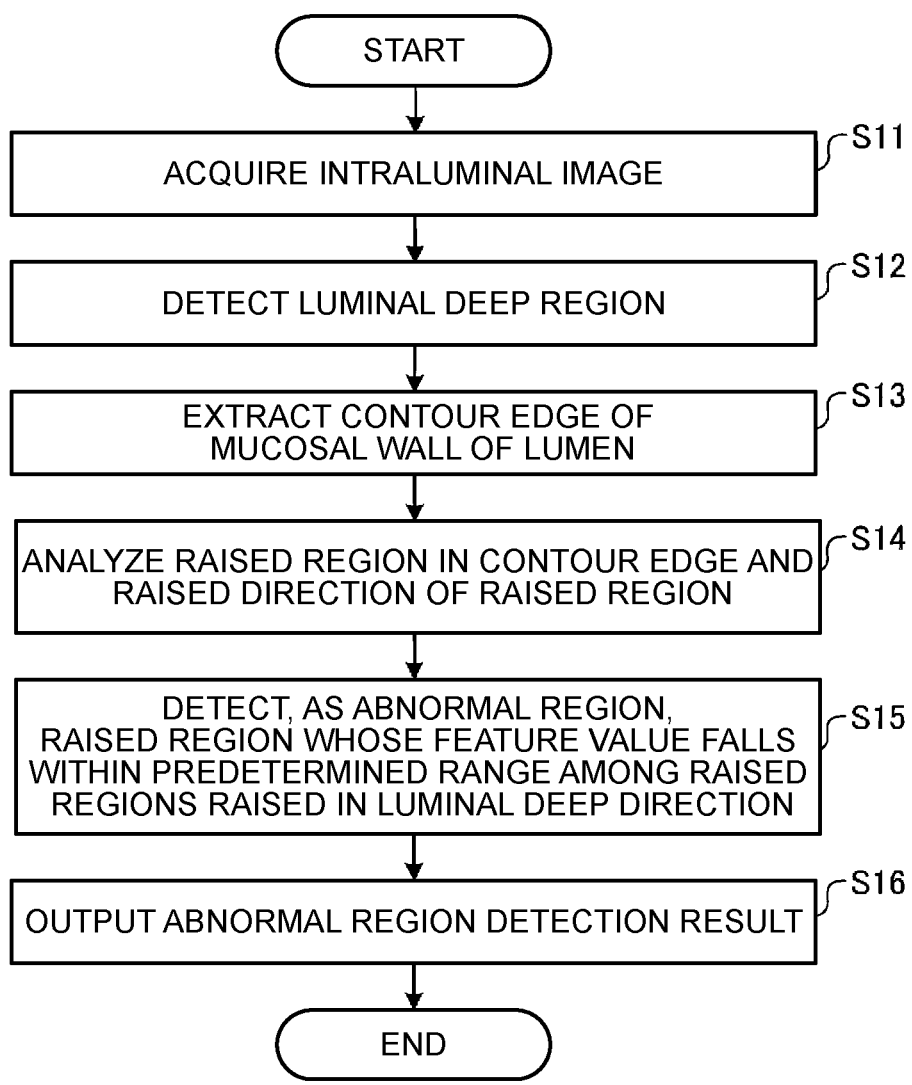
FIG. 14 is a flowchart illustrating an outline of processing performed by the image processing device according to Embodiment 2 of the present invention.

FIG. 14 is a flowchart illustrating an outline of processing performed by the image processing device 4. Processing steps S11 to S14 are the same as steps S1 to S4 in FIG. 4, respectively.

In step S15, the feature-value-of-raised-region calculating unit 511 calculates the feature value of a raised region raised in a luminal deep direction, and the abnormal region detecting unit 51 detects, as an abnormal region, a raised region whose calculated feature value falls within a predetermined range (step S15). Step S15 will be described in detail below.

The luminal deep direction calculating unit 241 and the region determination unit 242 perform like processing as that of steps S501 to S505 in Embodiment 1 (see FIG. 7) or steps S511 to S515 in Variation 1 of Embodiment 1 (see FIG. 12) to determine a raised region raised in the luminal deep direction. After that, the feature-value-of-raised-region calculating unit 511 calculates the feature value of the raised region. The abnormal region detecting unit 51 detects, as an abnormal region, a raised region whose feature value falls within the predetermined range.

In step S16 following step S15, the arithmetic unit 5 outputs the abnormal region detection result (step S16). Thus, a series of processing performed by the image processing device according to Embodiment 2 is ended.

According to Embodiment 2 of the present invention described above, a contour edge region having a raised shape in the direction of the luminal deep region is detected as an abnormal region. Therefore, the abnormal region can be detected with high accuracy while suppressing the erroneous detection of a normal contour edge as an abnormal region.

Further, according to Embodiment 2, relatively small regions among the regions detected from the luminal deep direction and the raised directions of raised regions are eliminated. Therefore, the erroneous detection of an abnormal region in a contour edge can further be suppressed.

Embodiment 3 of the present invention uses the fact that there is a difference in raised region surrounding pixel value information between an abnormal region and a case where a contour edge of a rim of a mucosal fold, which is not on the side of a luminal deep portion, is raised in the luminal deep direction to further increase the detection accuracy of the abnormal region. More specifically, when the contour edge of the rim of the mucosal fold, which is not on the side of the luminal deep portion, is raised in the luminal deep direction, Embodiment 3 uses the fact that mucous membrane over a fold on the side of the raised direction of a raised region has a higher pixel value than that of mucous membrane under an opposite fold (rim) because of a closer image capturing distance, while the pixel values of the abnormal region show a reverse trend. Thus, the detection accuracy of the abnormal region is further increased.

Figure 15:
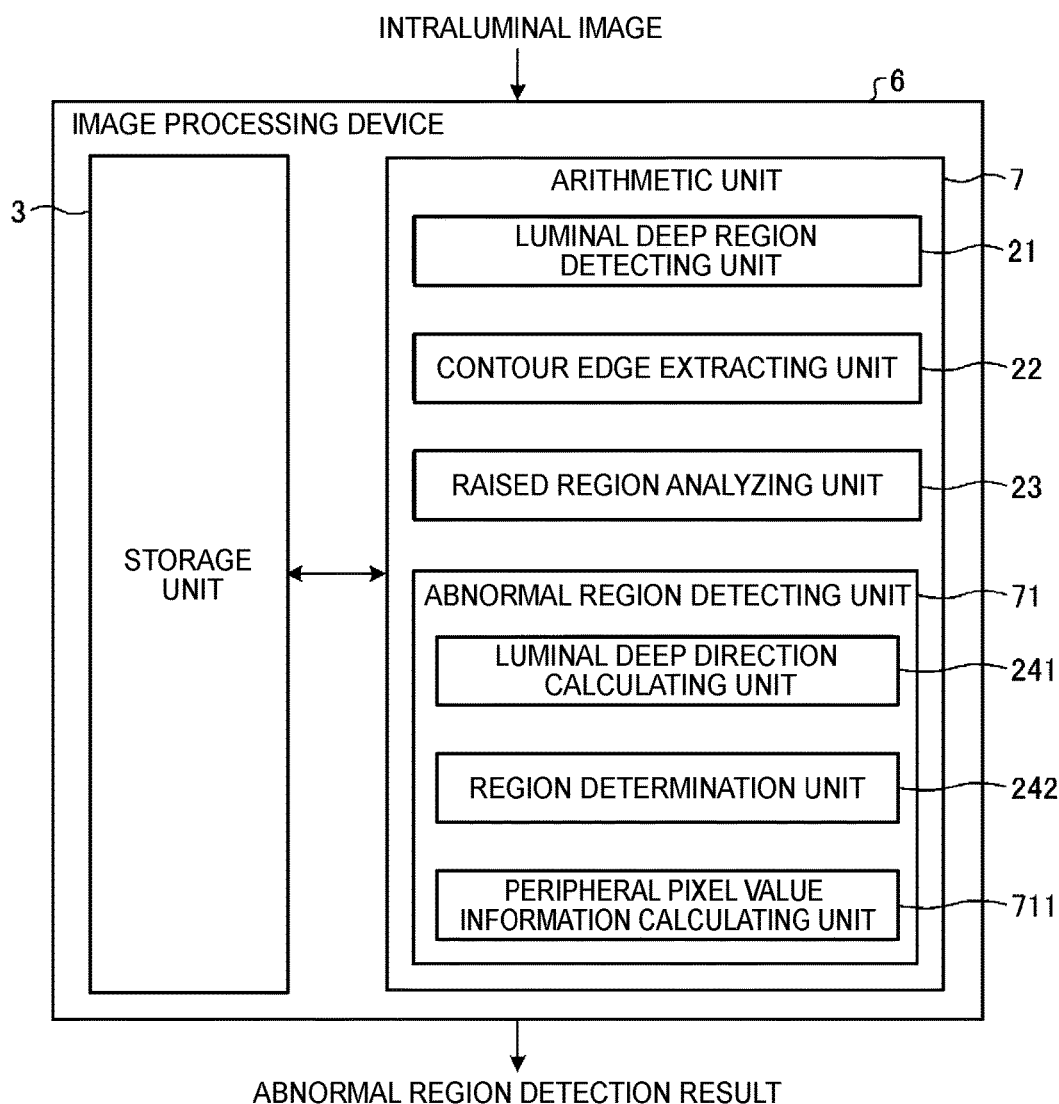
FIG. 15 is a block diagram illustrating the functional configuration of an image processing device according to Embodiment 3 of the present invention.

FIG. 15 is a block diagram illustrating the functional configuration of an image processing device according to Embodiment 3. An image processing device 6 illustrated in FIG. 15 includes an arithmetic unit 7 and a storage unit 3. In the following description, like components as those in the arithmetic unit 2 of the image processing device 1 according to Embodiment 1 are given the same reference numerals.

The arithmetic unit 7 has a luminal deep region detecting unit 21, a contour edge extracting unit 22, a raised region analyzing unit 23, and an abnormal region detecting unit 71. The abnormal region detecting unit 71 has a luminal deep direction calculating unit 241, a region determination unit 242, and a peripheral pixel value information calculating unit 711 that calculates raised region surrounding pixel value information.

The peripheral pixel value information calculating unit 711 calculates the amount of change between the pixel value of a region located on the raised direction side of a raised region and the pixel value of a region located in a direction opposite to the region across the raised region. For example, the peripheral pixel value information calculating unit 711 calculates a difference obtained by subtracting, from the pixel value of a region located on the raised direction side of a raised region, the pixel value of a region located on a side opposite to the region across the raised region. When the peripheral pixel value information calculating unit 711 calculates pixel values, it is more preferred that pixel values of a low-absorption wavelength component correlated with the image capturing distance should be used because relatively high accuracy can be obtained.

Figure 16:
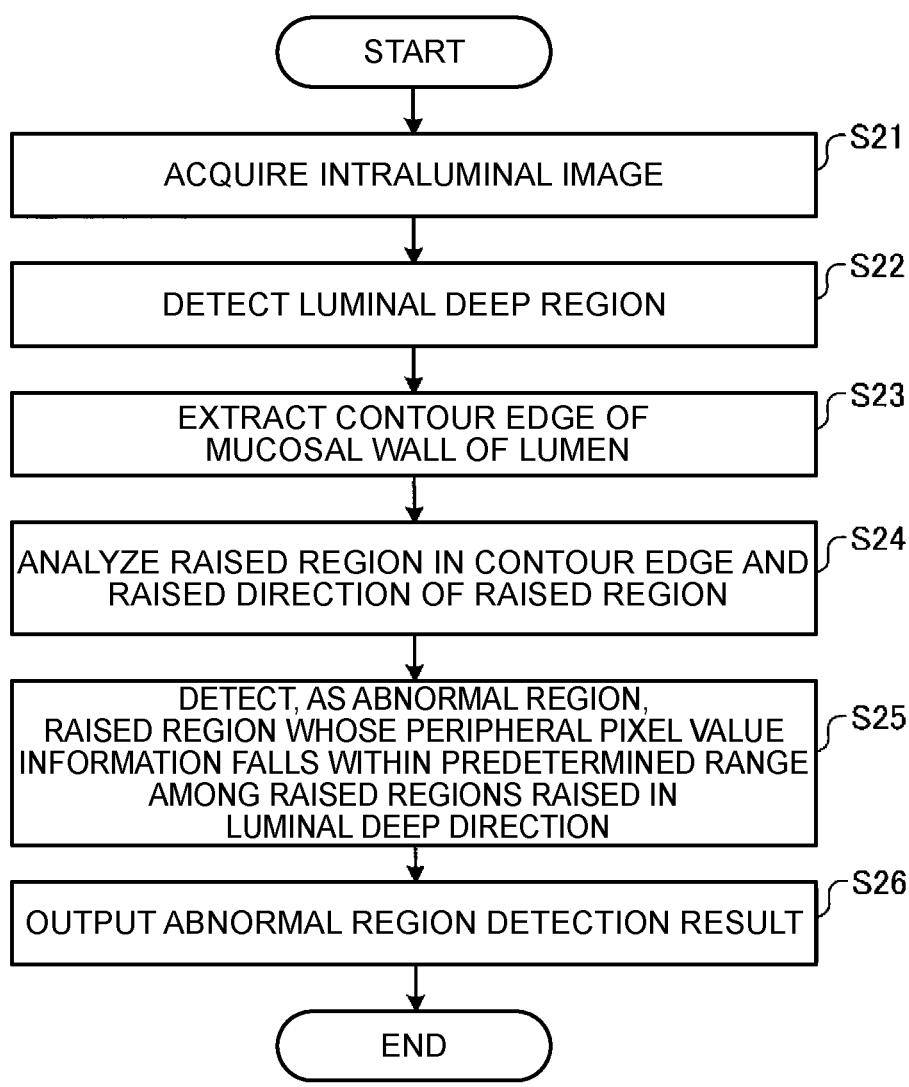
FIG. 16 is a flowchart illustrating an outline of processing performed by the image processing device according to Embodiment 3 of the present invention.

FIG. 16 is a flowchart illustrating an outline of processing performed by the image processing device 6. Processing steps S21 to S24 are the same as steps S1 to S4 in FIG. 4, respectively.

In step S25, after a raised region in a contour edge and the raised direction of the raised region are analyzed, the abnormal region detecting unit 71 detects, as an abnormal region, a raised region whose peripheral pixel value information falls within a predetermined range among raised regions raised in the luminal deep direction (step S25).

The luminal deep direction calculating unit 241 and the region determination unit 242 perform like processing as steps S501 to S505 in Embodiment 1 (see FIG. 7) or steps S511 to S515 in Variation 1 of Embodiment 1 (see FIG. 12) to determine the raised region raised in the luminal deep direction.

After that, the peripheral pixel value information calculating unit 711 calculates raised region surrounding pixel value information. When the peripheral pixel value information calculating unit 711 calculates a difference as mentioned above, the sign (plus or minus) is different between a normal contour edge region and the abnormal region. Specifically, the difference in the normal contour edge region becomes positive, while the difference in the abnormal region becomes negative.

Based on the calculation result of the peripheral pixel value information calculating unit 711, for example, the abnormal region detecting unit 71 detects, as the abnormal region, a region in which the difference becomes negative as mentioned above.

In step S26 following step S25, the arithmetic unit 7 outputs the abnormal region detection result (step S26). Thus, a series of processing performed by the image processing device according to Embodiment 3 is ended.

According to Embodiment 3 of the present invention described above, a contour edge region having a raised shape in the direction of the luminal deep region is detected as an abnormal region. Therefore, the abnormal region can be detected with high accuracy while suppressing the erroneous detection of a normal contour edge as being abnormal.

Further, according to Embodiment 3, since the abnormal region is detected by taking into account a change in raised region surrounding pixel value as well, the abnormal region can be detected with higher accuracy.

In Embodiment 4 of the present invention, dark parts such as a luminal deep portion, bright parts such as specular reflection, residues, bubbles, and the like contained in an intraluminal image are excluded as non-inspected regions before extraction of a contour edge to further increase the detection accuracy of an abnormal region.

Figure 17:
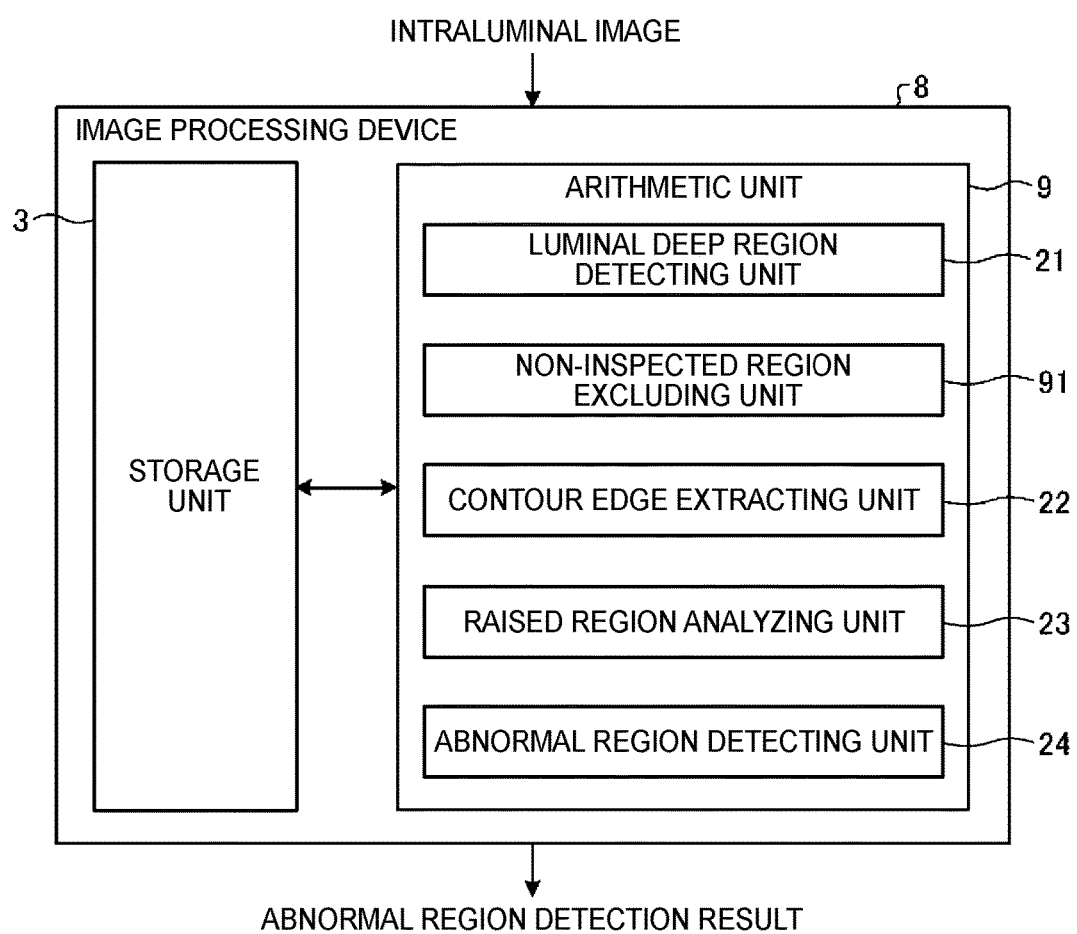
FIG. 17 is a block diagram illustrating the functional configuration of an image processing device according to Embodiment 4 of the present invention.

FIG. 17 is a block diagram illustrating the functional configuration of an image processing device according to Embodiment 4. An image processing device 8 illustrated in FIG. 17 includes an arithmetic unit 9 and a storage unit 3. In the following description, like components as those in the arithmetic unit 2 of the image processing device 1 according to Embodiment 1 are given the same reference numerals.

The arithmetic unit 9 has a luminal deep region detecting unit 21, a non-inspected region excluding unit 91, a contour edge extracting unit 22, a raised region analyzing unit 23, and an abnormal region detecting unit 24.

The non-inspected region excluding unit 91 identifies non-mucosal regions (dark parts, bright parts, residues, bubbles, and the like) based on information on color, frequency, shape, etc. to exclude these identified non-mucosal regions as non-inspected regions. The non-inspected region excluding unit 91 identifies non-mucosal regions by applying techniques disclosed, for example, in Japanese Patent Application Laid-Open No. 2011-234931 (dark part, bright part), Japanese Patent Application Laid-Open No. 2012-143340 (residue), and Japanese Patent Application Laid-Open No. 2007-313119 (bubble).

Figure 18:
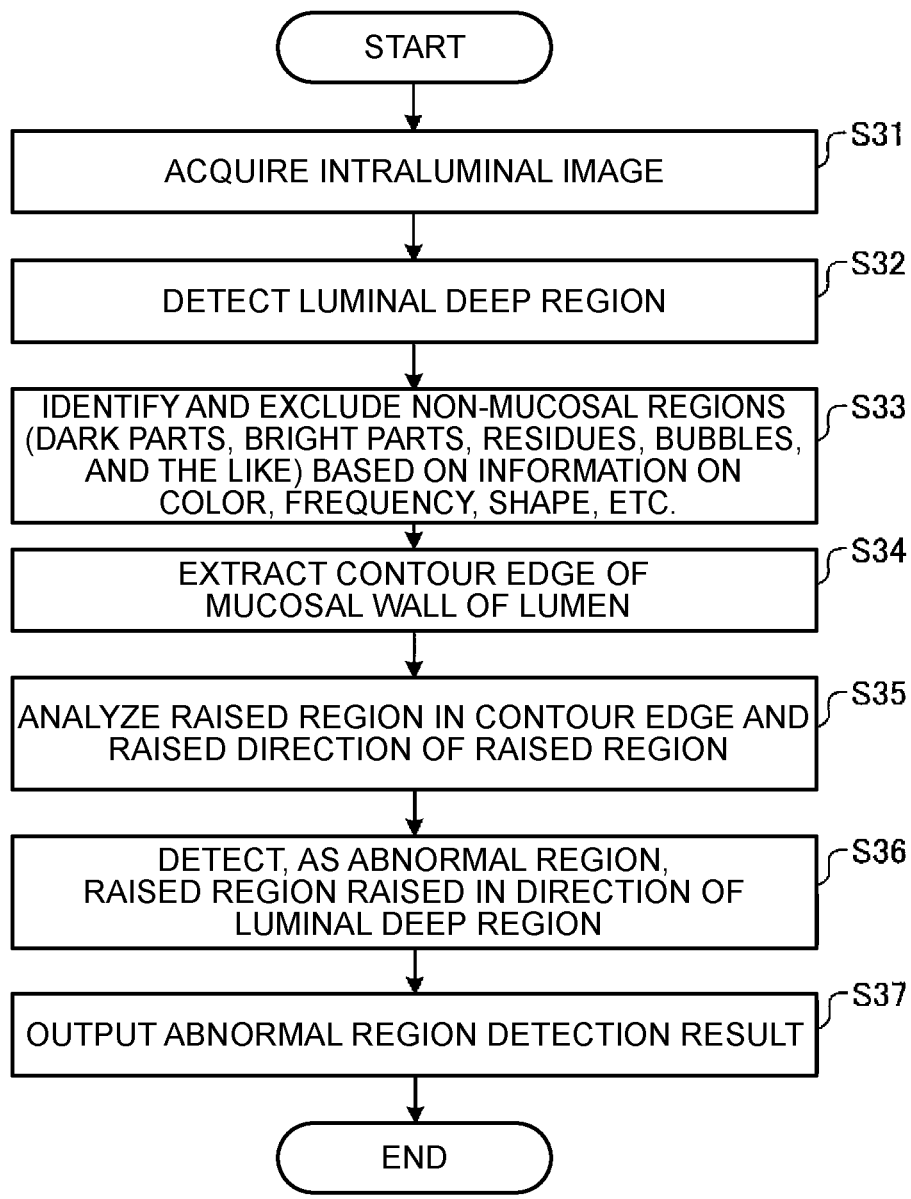
FIG. 18 is a flowchart illustrating an outline of processing performed by the image processing device according to Embodiment 4 of the present invention.

FIG. 18 is a flowchart illustrating an outline of processing performed by the image processing device 8. Steps S31 and S32 correspond to steps S1 and S2 in FIG. 4, respectively.

After step S32, the non-inspected region excluding unit 91 identifies non-mucosal regions (dark parts, bright parts, residues, bubbles, and the like) based on information on color, frequency, shape, etc. to exclude the identified non-mucosal regions as non-inspected regions (step S33).

Processing steps S34 to S37 sequentially correspond to processing steps S3 to S6 in FIG. 4.

According to Embodiment 4 of the present invention described above, a contour edge region having a raised shape in the direction of the luminal deep region is detected as an abnormal region. Therefore, the abnormal region can be detected with high accuracy while suppressing the erroneous detection of a normal contour edge as being abnormal.

Further, according to Embodiment 4, non-inspected regions are excluded before the extraction of the contour edge region. Therefore, the abnormal region can be detected with higher accuracy.

Note that the functional configuration of the non-inspected region excluding unit 91 can also be provided in the image processing device according to any of Embodiments 1 to 3 mentioned above.

While the modes for carrying out the present invention have been described, the present invention is not limited only to Embodiments 1 to 4 mentioned above. For example, when an abnormal region is detected, an arc-shaped region existing on the same side as a luminal deep region with reference to a straight line passing through the chord of the arc-shaped region may be detected as the abnormal region.

In addition to an endoscopic image for a living body, the present invention can also be applied to an intraductal image of virtual endoscope generated in CT colonography, and an intraluminal image captured using an industrial endoscope.

Figure 19:
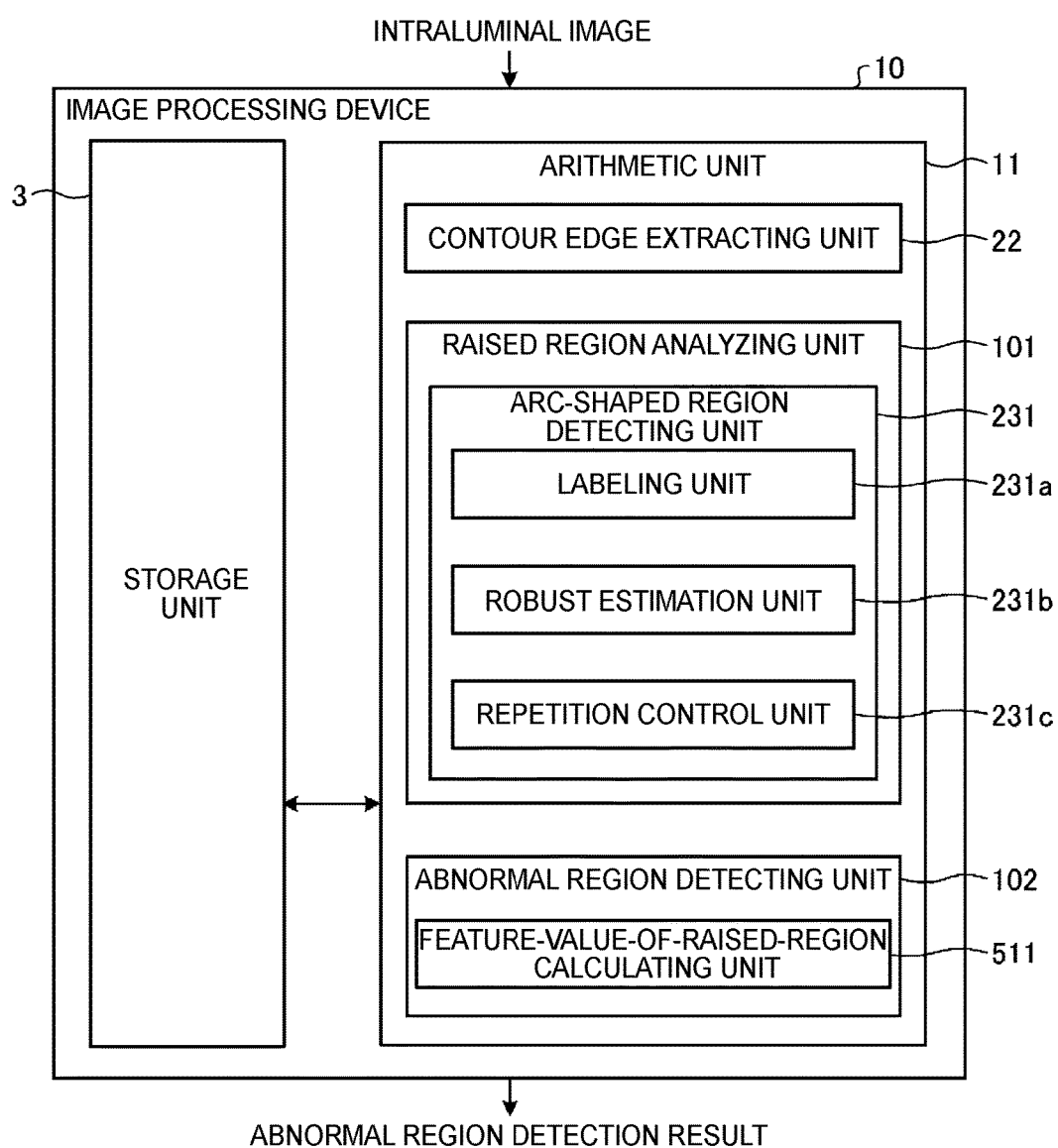
FIG. 19 is a block diagram illustrating the functional configuration of an image processing device according to a different embodiment.

FIG. 19 is a block diagram illustrating the functional configuration of an image processing device according to a different embodiment. An image processing device 10 illustrated in the figure includes an arithmetic unit 11 and a storage unit 3. In the following description, like components as those in the arithmetic unit 2 of the image processing device 1 are given the same reference numerals.

The arithmetic unit 11 has a contour edge extracting unit 22, a raised region analyzing unit 101, and an abnormal region detecting unit 102. The raised region analyzing unit 101 has an arc-shaped region detecting unit 231. The arc-shaped region detecting unit 231 has a labeling unit 231*a*, a robust estimation unit 231*b*, and a repetition control unit 231*c*. The abnormal region detecting unit 102 has a feature-value-of-raised-region calculating unit 511.

Figure 20:
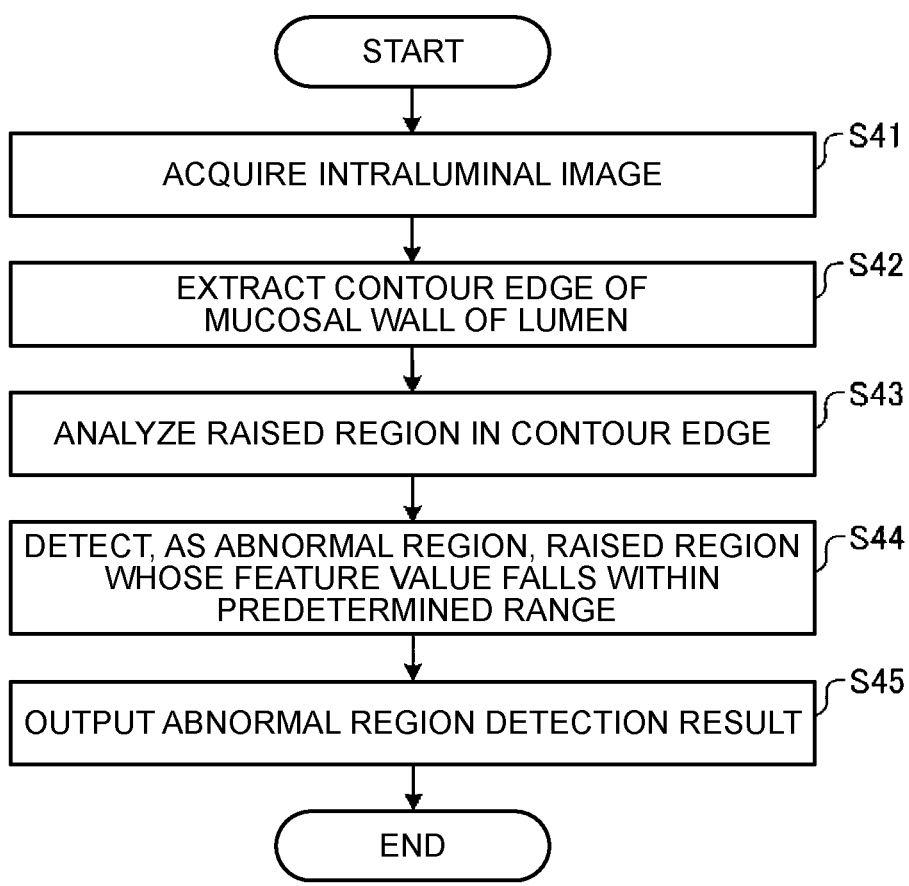
FIG. 20 is a flowchart illustrating an outline of processing performed by the image processing device according to the different embodiment.

FIG. 20 is a flowchart illustrating an outline of processing performed by the image processing device 10. Processing steps S41 and S42 are the same as processing steps S1 and S3 in FIG. 4, respectively.

In step S43, the arc-shaped region detecting unit 231 in the raised region analyzing unit 101 analyzes a raised region in a contour edge (step S43). After the arc-shaped region detecting unit 231 sequentially executes processing steps S401 to S404 illustrated in FIG. 6, raised region analysis processing is ended.

In step S44, the feature-value-of-raised-region calculating unit 511 calculates the feature value of each raised region, and the abnormal region detecting unit 102 detects, as an abnormal region, a raised region whose calculated feature value falls within a predetermined range (step S44).

In step S45, the arithmetic unit 11 outputs the abnormal region detection result (step S45). Thus, a series of processing performed by the image processing device 10 is ended.

According to the image processing device 10 described above, since one contour edge is split into plural arc shapes to determine an abnormal region, an abnormal tissue edge can be detected with high accuracy.

Note that a unit with the raised-direction-of-split-edge calculating unit 262 eliminated from the raised region analyzing unit 26 illustrated in FIG. 8 can also be adopted as the raised region analyzing unit in the image processing device 10. In other words, the raised region analyzing unit in this case has an edge splitting unit 261. The edge splitting unit 261 has an edge coordinate acquiring unit 261*a*, a curvature change analyzing unit 261*b*, and a splitting unit 261*c*.

Further, the abnormal region detecting unit in the image processing device 10 may have the function of the peripheral pixel value information calculating unit 711 illustrated in FIG. 15. In this case, the abnormal region detecting unit can detect an abnormal region by taking into account the peripheral pixel value information as well.

Further, the function of the non-inspected region excluding unit 91 described in Embodiment 4 may be implemented in the image processing device 10. In this case, the abnormal region can be detected with higher accuracy.

DESCRIPTION OF REFERENCE NUMERALS

Example embodiments of the present invention relate to an image processing device. The device comprises a deep region detecting unit that detects a deep region in an intraductal image, a contour edge extracting unit that extracts a contour edge of an inner wall of a duct, a raised region analyzing unit that analyzes a raised region in the contour edge and a raised direction of the raised region, and an abnormal region detecting unit that detects, as an abnormal region, a raised region raised in a direction of the deep region.

The raised region analyzing unit can have an arc-shaped region detecting unit that detects an arc-shaped region in the contour edge, and an arc-shaped raised direction calculating unit that calculates a raised direction of the arc-shaped region.

The arc-shaped region detecting unit can have a robust estimation unit that detects an arc-shaped region by robust estimation based on pixels in the contour edge, and a repetition control unit that performs control over regions other than the detected arc-shaped region to repeat detection of the arc-shaped region by the robust estimation.

The arc-shaped region detecting unit can have a labeling unit that labels each contour edge so that the same label will be put on only the contour edges to be connected, the robust estimation unit detects the arc-shaped region based on pixels in the contour edges of the same label, and the repetition control unit performs control over regions other than the detected arc-shaped region to repeat the labeling and the detection of the arc-shaped region.

The raised region analyzing unit can have an edge splitting unit that splits the contour edge based on a curved direction of the contour edge, and a raised-direction-of-split-edge calculating unit that calculates a raised direction of each split edge.

The edge splitting unit can have an edge coordinate acquiring unit that acquires, in order of connection, edge coordinates as coordinates of each of pixels forming each edge, a curvature change analyzing unit that analyzes a change in signed curvature with respect to the contour edge based on the coordinates of sample pixels placed at predetermined intervals among the acquired edge coordinates, and a splitting unit that splits the contour edge at a position of sign inversion of the signed curvature.

The abnormal region detecting unit can have a deep direction calculating unit that calculates a deep direction based on the deep region detection result and the raised region analysis result, and a region determination unit that determines the raised region raised in the deep direction, whereby the raised region determined by the region determination unit is detected as an abnormal region.

The deep direction calculating unit can have a representative-position-of-deep-region calculating unit that calculates a representative position of the deep region, and a representative position direction calculating unit that calculates a direction from a representative position of each raised region to the representative position of the deep region.

The deep direction calculating unit can have a distance converted image creating unit that creates a distance converted image from the deep region, and a gradient direction calculating unit that calculates a gradient direction of each raised region at a representative position in the distance converted image.

The region determination unit can have an angle calculation unit that calculates an angle between two directions of a raised direction of the raised region and the deep direction, whereby when the angle is less than or equal to a predetermined threshold value, a raised region raised in the deep direction is determined.

The region determination unit can have an inner product calculating unit that calculates an inner product of unit directional vectors in two directions of a raised direction of the raised region and the deep direction, whereby when the inner product is more than or equal to a predetermined threshold value, a raised region raised in the deep direction is determined.

The abnormal region detecting unit further can have a feature-value-of-raised-region calculating unit that calculates a feature value of the raised region, and a raised region whose feature value falls predetermined range among raised regions raised in the deep direction is detected as an abnormal region.

The feature-value-of-raised-region calculating unit can calculate, as a feature value of the raised region, any one of values correlated with a length, area, and raised amount of the raised region.

The abnormal region detecting unit can have a peripheral pixel value information calculating unit that calculates peripheral pixel value information on the raised region, and a raised region whose peripheral pixel value information falls within a predetermined range among raised regions raised in the deep direction is detected as an abnormal region.

The peripheral pixel value information calculating unit can calculate changes in pixel value of a region located on the raised direction side of the raised region and a region located in a direction opposite to the region across the raised region.

The deep region detecting unit can have a low-absorption wavelength component selecting unit that selects an image of a low-absorption wavelength component as a wavelength component whose degree of absorption/scattering in a living body is lowest, an edge surrounding region eliminating unit that eliminates pixels of an edge surrounding region in the image of the low-absorption wavelength component, and a low pixel-value region detecting unit that detects a region having a relatively low pixel value in the image of the low-absorption wavelength component after the pixels of the edge surrounding region are eliminated, whereby the deep region is detected based on the result of the low pixel-value region detecting unit.

The image processing device can comprise a non-inspected region excluding unit that excludes any of regions of specular reflection, dark parts, bubbles, and residues from the intraductal image.

Example embodiments of the present invention relate to an image processing method. The method comprises a deep region detecting step of detecting a deep region in an intraductal image, a contour edge extracting step of extracting a contour edge of an inner wall of a duct, a raised region analyzing step of analyzing a raised region in the contour edge and a raised direction of the raised region, and an abnormal region detecting step of detecting, as an abnormal region, a raised region raised in a direction of the deep region.

Example embodiments of the present invention relate to an image processing program. The program causes a computer to execute a deep region detecting step of detecting a deep region in an intraductal image, a contour edge extracting step of extracting a contour edge of an inner wall of a duct, a raised region analyzing step of analyzing a raised region in the contour edge and a raised direction of the raised region, and an abnormal region detecting step of detecting, as an abnormal region, a raised region raised in a direction of the deep region.

What is claimed is:

1. An image processing apparatus comprising:
a processor; and
memory storing instructions that when executed on the processor cause the processor to perform the operations of:
detecting a deep region of a duct in an image;
extracting a plurality of contour edges of an inner wall of the duct in the image;
identifying a plurality of convex regions among the plurality of contour edges;
analyzing a respective curvature of each of the plurality of convex regions to identify a convex direction for each of the plurality of convex regions; and detecting, as an abnormal region, a convex region having a convex direction directed toward the deep region so as to enable the image processing apparatus to detect an abnormal tissue edge with high accuracy while suppressing an erroneous determination of a normal tissue edge to be abnormal.

2. The image processing apparatus according to claim 1, wherein the memory further stores instructions that when executed on the processor cause the process to perform the operations of: detecting an arc-shaped region in the contour edge; and calculating a convex direction of the arc-shaped region.

3. The image processing apparatus according to claim 2 wherein the memory further stores instructions that when executed on the processor cause the process to perform the operations of: detecting the arc-shaped region by robust estimation based on pixels in the contour edge; and repeating detection of the arc-shaped region by robust estimation over regions other than the detected arc-shaped region.

4. The image processing apparatus according to claim 3, wherein the memory further stores instructions that when executed on the processor cause the process to perform the operations of: labeling each contour edge so that the same label will be put on only the contour edges to be connected; detecting the arc-shaped region based on pixels in the contour edges of the same label; and repeating the labeling and the detecting arc-shaped regions.

5. The image processing apparatus according to claim 1, wherein the memory further stores instructions that when executed on the processor cause the process to perform the operations of: splitting the contour edge based on a curved direction of the contour edge; and calculating a convex direction of each split edge.

6. The image processing apparatus according to claim 5, wherein the memory further stores instructions that when executed on the processor cause the process to perform the operations of: acquiring, in order of connection, edge coordinates as coordinates of each of a plurality of pixels forming each edge; analyzing a change in signed curvature with respect to the contour edge based on the coordinates of sample pixels at intervals among the acquired edge coordinates; and splitting the contour edge at a position of sign inversion of the signed curvature.

7. The image processing apparatus according to claim 1, wherein the memory further stores instructions that when executed on the processor cause the process to perform the operations of: calculating a deep direction based on the detected deep region and the analyzed convex region; determining the convex region is raised in a convex direction toward the deep direction; and detecting the convex region as an abnormal region.

8. The image processing apparatus according to claim 7, wherein the memory further stores instructions that when executed on the processor cause the process to perform the operations of: calculating a representative position of the deep region; and calculating a direction from a respective representative position of each convex region to the representative position of the deep region.

9. The image processing apparatus according to claim 7, wherein the memory further stores instructions that when executed on the processor cause the process to perform the operations of: creating a distance converted image from the deep region; and calculating a gradient direction of each convex region at a representative position in the distance converted image.

10. The image processing apparatus according to claim 7, wherein the memory further stores instructions that when executed on the processor cause the process to perform the operations of: calculating an angle between a convex direction of a convex region and a direction of the deep direction; and detecting the convex region is raised in a direction of the deep region if the angle is less than or equal to a threshold value.

11. The image processing apparatus according to claim 7, wherein the memory further stores instructions that when executed on the processor cause the process to perform the operations of: calculating an inner product of unit directional vectors in two directions of a convex direction of the convex region and the deep direction; and detecting the convex region is raised in a direction of the deep direction if the inner product is greater than or equal to a threshold value.

12. The image processing apparatus according to claim 7, wherein the memory further stores instructions that when executed on the processor cause the process to perform the operations of: calculating a feature value of the convex region; and detecting the convex region as an abnormal region if the feature value is in an identified range of feature values among convex regions raised in the deep direction.

13. The image processing apparatus according to claim 12, wherein the memory further stores instructions that when executed on the processor cause the process to perform the operation of calculating, as the feature value of the convex region, a correlated value selected from the group consisting of length, area, and raised amount of the convex region.

14. The image processing apparatus according to claim 7, wherein the memory further stores instructions that when executed on the processor cause the process to perform the operations of: calculating a peripheral pixel value of the convex region; and detecting the convex region as an abnormal region if the peripheral pixel value is in an identified range of peripheral pixel values among convex regions raised in the deep direction.

15. The image processing apparatus according to claim 14, wherein the memory further stores instructions that when executed on the processor cause the process to perform the operation of calculating changes in peripheral pixel value of a region located on the convex direction side of the convex region and a region located in a direction opposite to the region across the convex region.

16. The image processing apparatus according to claim 1, wherein the memory further stores instructions that when executed on the processor cause the process to perform the operations of: selecting an image of a low-absorption wavelength component as a wavelength component having a lowest degree of absorption/scattering in a living body; eliminating pixels of an edge surrounding region in the image of the low-absorption wavelength component; detecting a region having a low pixel value relative to WHAT in the image of the low-absorption wavelength component after the pixels of the edge surrounding region are eliminated; and detecting the deep region based on the region having the low pixel value.

17. The image processing apparatus according to claim 1 wherein the memory further stores instructions that when executed on the processor cause the process to perform the operation of excluding regions of specular reflection, dark parts, bubbles, and residues from the image.

18. A method of operating an image processing apparatus comprising:
 detecting a deep region of a duct in an image;
 extracting a contour edge of an inner wall of the duct in the image;

identifying a plurality of convex regions among the plurality of contour edges;

analyzing a respective curvature of each of the plurality of convex regions to identify a convex direction for each of the plurality of convex regions; and detecting, as an abnormal region, a convex region having a convex direction directed toward a direction of the deep region so as to enable the image processing apparatus to detect an abnormal tissue edge with high accuracy while suppressing an erroneous determination of a normal tissue edge to be abnormal.

19. The method of claim 18, wherein extracting a plurality of contour edges of an inner wall of the duct in the image comprises: detecting an arc-shaped region in the contour edge; and calculating a convex direction of the arc-shaped region.

20. The method of claim 19, wherein detecting an arc-shaped region in the contour edge comprises: detecting the arc-shaped region by robust estimation based on pixels in the contour edge; and repeating detection of the arc-shaped region by robust estimation over regions other than the detected arc-shaped region.

21. The method of claim 20 further comprising: labeling each contour edge so that the same label will be put on only the contour edges to be connected; detecting the arc-shaped region based on pixels in the contour edges of the same label; and repeating the labeling and the detecting arc-shaped regions.

22. The method of claim 18, wherein extracting a plurality of contour edges of an inner wall of the duct in the image comprises: splitting the contour edge based on a curved direction of the contour edge; and calculating a convex direction of each split edge.

23. The method of claim 22, wherein splitting the contour edge based on a curved direction of the contour edge comprises: acquiring, in order of connection, edge coordinates as coordinates of each of a plurality of pixels forming each edge; analyzing a change in signed curvature with respect to the contour edge based on the coordinates of sample pixels at intervals among the acquired edge coordinates; and splitting the contour edge at a position of sign inversion of the signed curvature.

24. The method of claim 18, wherein detecting, as an abnormal region, a convex region having a convex direction directed toward the deep region comprises: calculating a deep direction based on the detected deep region and the analyzed convex region; determining the convex region is raised in a convex direction toward the deep direction; and detecting the convex region as an abnormal region.

25. The method of claim 24, wherein calculating a deep direction based on the detected deep region and the analyzed convex region comprises: calculating a representative position of the deep region; and calculating a direction from a respective representative position of each convex region to the representative position of the deep region.

26. The method of claim 24, wherein calculating a deep direction based on the detected deep region and the analyzed convex region comprises: creating a distance converted image from the deep region; and calculating a gradient direction of each convex region at a representative position in the distance converted image.

27. The method of claim 24, wherein determining the convex region is raised in a convex direction toward the deep direction comprises: calculating an angle between a convex direction of a convex region and a direction of the deep direction; and detecting the convex region is raised in a direction of the deep region if the angle is less than or equal to a threshold value.

28. The method of claim 24, wherein determining the convex region is raised in a convex direction toward the deep direction comprises: calculating an inner product of unit directional vectors in two directions of a convex direction of the convex region and the deep direction; and detecting the convex region is raised in a direction of the deep direction if the inner product is greater than or equal to a threshold value.

29. The method of claim 24, wherein detecting, as an abnormal region, a convex region having a convex direction directed toward the deep region comprises: calculating a feature value of the convex region; and detecting the convex region as an abnormal region if the feature value is in an identified range of feature values among convex regions raised in the deep direction.

30. The method of claim 29, wherein calculating a feature value of the convex region comprises calculating, as the feature value of the convex region, a correlated value selected from the group consisting of length, area, and raised amount of the convex region.

31. The method of claim 24, wherein detecting, as an abnormal region, a convex region having a convex direction directed toward the deep region comprises: calculating a peripheral pixel value of the convex region; and detecting the convex region as an abnormal region if the peripheral pixel value is in an identified range of peripheral pixel values among convex regions raised in the deep direction.

32. The method of claim 31, wherein calculating a peripheral pixel value of the convex region comprises calculating changes in peripheral pixel value of a region located on the convex direction side of the convex region and a region located in a direction opposite to the region across the convex region.

33. The method of claim 18, wherein detecting a deep region of a duct in an image comprises: selecting an image of a low-absorption wavelength component as a wavelength component having a lowest degree of absorption/scattering in a living body; eliminating pixels of an edge surrounding region in the image of the low-absorption wavelength component; detecting a region having a low pixel value relative to WHAT in the image of the low-absorption wavelength component after the pixels of the edge surrounding region are eliminated; and detecting the deep region based on the region having the low pixel value.

34. The method of claim 18 further comprising excluding regions of specular reflection, dark parts, bubbles, and residues from the image.

35. A computer program product including a non-transitory computer readable medium having computer program code encoded thereon that when executed by a processor of a computer causes the computer to perform image process of an image processing apparatus, the computer program code comprising:

computer program code for detecting a deep region of a duct in an image;

computer program code for extracting a contour edge of an inner wall of the duct in the image;

computer program code for identifying a plurality of convex regions among the plurality of contour edges;

computer program code for analyzing a respective curvature of each of the plurality of convex regions to identify a convex direction for each of the plurality of convex regions; and computer program code for detecting, as an abnormal region, a convex region having a convex direction directed toward a direction of the deep region so as to enable the image processing apparatus to detect an abnormal tissue edge with high accuracy while suppressing an erroneous determination of a normal tissue edge to be abnormal.

\* \* \* \* \*